US006828435B2

(12) United States Patent
Koster et al.

(10) Patent No.: US 6,828,435 B2
(45) Date of Patent: Dec. 7, 2004

(54) COMBINATORIAL PROTECTING GROUP STRATEGY FOR MULTIFUNCTIONAL MOLECULES

(75) Inventors: Hubert Koster, Hamburg (DE); Eckart Leikauf, Hamburg (DE)

(73) Assignee: HK Pharmaceuticals, Inc., San Diego, CA (US)

( * ) Notice: Subject to any disclaimer, the term of this patent is extended or adjusted under 35 U.S.C. 154(b) by 72 days.

(21) Appl. No.: 09/171,625

(22) PCT Filed: Apr. 17, 1997

(86) PCT No.: PCT/US97/06509

§ 371 (c)(1),
(2), (4) Date: Jul. 2, 1999

(87) PCT Pub. No.: WO97/41139

PCT Pub. Date: Nov. 6, 1997

(65) Prior Publication Data

US 2003/0194741 A1 Oct. 16, 2003

Related U.S. Application Data

(60) Provisional application No. 60/015,699, filed on Apr. 17, 1996.

(51) Int. Cl.[7] .......................... C07H 21/04; C07H 21/02; G01N 33/543; C12Q 1/68
(52) U.S. Cl. .................. 536/25.1; 536/23.1; 536/25.31; 435/6; 435/DIG. 1; 435/DIG. 34; 435/DIG. 35; 435/DIG. 40; 435/DIG. 46
(58) Field of Search .............................. 536/25.1, 23.1; 435/6, DIG. 1, DIG. 34, DIG. 35, DIG. 40

(56) References Cited

U.S. PATENT DOCUMENTS

| 5,143,854 A | 9/1992 | Pirrung et al. ............... 436/518 |
| 5,410,068 A | 4/1995 | Coull et al. .................. 548/545 |
| 5,503,980 A | 4/1996 | Cantor .......................... 435/6 |
| 5,547,835 A | 8/1996 | Köster ........................... 435/6 |
| 5,582,981 A | 12/1996 | Toole et al. .................... 435/6 |
| 5,605,798 A | 2/1997 | Koster ........................... 435/6 |
| 5,614,622 A | 3/1997 | Iyer et al. ................. 536/25.33 |
| 5,622,824 A | 4/1997 | Koster ........................... 435/6 |
| 5,631,134 A | 5/1997 | Cantor .......................... 435/6 |
| 5,652,358 A | 7/1997 | Pfleiderer et al. .......... 536/25.3 |
| 5,688,642 A | 11/1997 | Chrisey et al. ................. 435/6 |
| 5,691,141 A | 11/1997 | Koster ........................... 435/6 |
| 5,763,599 A | 6/1998 | Pfleiderer et al. .......... 536/55.3 |
| 5,777,324 A | 7/1998 | Hillenkamp ................ 250/288 |
| 5,795,714 A | 8/1998 | Cantor et al. ................... 435/6 |
| 5,851,765 A | 12/1998 | Koster ........................... 435/6 |
| 5,872,003 A | 2/1999 | Koster ..................... 435/283.1 |
| 5,900,036 A | 5/1999 | Mossadegh et al. .......... 65/384 |

FOREIGN PATENT DOCUMENTS

| DE | 3644346 | 5/1987 | |
| WO | 8504674 | 10/1985 | ........... C12F/19/34 |
| WO | 8905616 | 6/1989 | ............. A61F/2/54 |
| WO | 9202533 | 2/1992 | |
| WO | 9503315 | 2/1995 | ............ C07H/3/06 |
| WO | 9741139 | 11/1997 | ........... C07H/19/06 |
| WO | 9820020 | 5/1998 | ........... C07H/21/00 |
| WO | 9603424 | 2/1999 | ............ C07K/1/04 |

OTHER PUBLICATIONS

Alper, J., Drug discovery on the assembly line, *Science*, 264:1399–1401 (1994).
Amarnath, V., et al., Chemical synthesis of oligonucleotides, *Chem. Rev.* 77:183–217 (1977).
Archady, R., Beaded polymer supports and gels: II. Physico–chemical criteria and functionalization, *Journal of Chromatography*, 586:199–219 (1991).
Beaucage, S.L., et al., The synthesis of modified oligonucleotides by the phosphoramidite approach and their applications, *Tetrahedron*, 49:6123–94 (1993).
Cohen, J.S., et al., The new genetic medicines, *Scientific American, International Edition*, pp. 76–84 (Dec. 1994).
Engels, J., Krankheit–Fehler in der Informationsübertragung, *Natur. Chem. Techn. Lab.*, 39:1250–54 (1991).
Froehler, B.C., et al., Synthesis of DNA via deoxynucleoside H–phosphonate intermediates, *Nucleic Acids Res.*, 14:5399–5407 (1984).
Froehler, B.C., et al., Nucleoside H–phosphonates: valuable intermediates in the synthesis of deoxyoligonucleotides, *Tetrahedron Lett.*, 27:469–72 (1986).
Garegg, P.J., et al., Nucleoside H–phosphonates. III. Chemical Synthesis of oligodeoxyribonucleotides, *Tetrahedron Lett.*, 27:4051–54 (1986).
Gershon, P.D., et al., Stable chelating linkage for reversible immobilization of oligohistidine tagged proteins in the BIA-core surface plasmon resonance detector, *Journal of Imunological Methods*, 183:65–76 (1995).
Gioeli, C., et al., The fluoren–9–ylmethoxycarbonyl group for the protection of hydroxy–groups; Its application in the synthesis of an octathymidylic acid fragment, *J. Chem. Soc., Chem. Commun.*, 672–74 (1982).
Gordon, E.M., et al., Applications of combinatorial technologies to drug discovery. 2. Combinatorial organic synthesis, library screening strategies, and future directions[1], *J. Med. Chem.*, 37:1385–1401 (1994).
Heikkila, J., et al., The 2–nitrophenylsulfenyl (Nps) group for the protection of amino functions of cytidine, adenosine, guanoside and their 2'–deoxysugar derivatives, *Acta Chem. Scand.*, B37:857–64 (1983).

(List continued on next page.)

*Primary Examiner*—Padmashri Ponnaluri
(74) *Attorney, Agent, or Firm*—Fish & Richardson P.C.; Stephanie L. Seidman; Dale L. Rieger

(57) ABSTRACT

The use of protection schemes and solid phase synthesis reactions to generate molecules of core structure M, which have a plurality of moieties, each of which can be individually deprotected or subsequently derivatized are provided. In one process, M is a multifunctional low molecular weight compound, such as a saccharide, aminosugar, deoxysugar, nucleoside, nucleotide, coenzyme, amino acid, lipid, steroid, vitamin, hormone, alkaloid, or small molecule drug. In another process, M is an oligomeric compound, such as an oligosaccharide, oligonucleotide, peptide or protein.

7 Claims, 3 Drawing Sheets

OTHER PUBLICATIONS

Himmelsbach, F., et al., The p–nitrophenylethyl (NPE) group: A versatile new blocking group for phosphate and aglycone protection in nucleosides and nucleotides, *Tetrahedron*, 40:59–72 (1984).

Hsiung, H.M., Improvements in the phosphotriester synthesis of deoxribooligonucleotides—The use of hindered primary amines and a new isolation procedure, *Tetrahedron Lett.*, 23:5119–22 (1982).

Johnson, W.S., et al., Studies in decarboxylation and lacto–enioc tautomerism. IV.[1] Paraconic acids[2], *J. Amer. Chem. Soc.*, 72:935–39 (1950).

Kharasch, N., et al., Derivatives of sulfenic acids. X. The reaction of 2,4–dinitrobenzenesulfenyl chloride with alcohols, *J. Amer. Chem. Soc.*, 75:2658–60 (1953).

Köster, H., et al., Some improvements of polymer oligodeoxynucleotide synthesis, *Natural Products Chemistry*, 9(14):227–37 (1984).

Leikauf, E., et al., A combinatorial protecting group strategy for oligonucleotide synthesis, *Tetrahedron*, 52(20):6913–30 (1996).

Leikauf, E., et al., A new colorimetric protecting group allowing deprotection under neutral conditions, *Tetrahedron*, 51(19):5557–62 (1995).

Nielsen, P., Sequence–selective recognition of DNA by strand displacement with a thymine–substituted polyamide, *Science*, 254:1497 (1991).

Nielsen, P., et al., Incorporation of (R)– and (S)–3',4'–seco–thymidine into oligodeoxynucleotides: hybridization properties and enzymatic stability, *Nucleic Acids Res.*, 22:703–10 (1994).

Ogilvie, K.K., The tert–butyldimethylsilyl group as a protecting group in deoxynucleosides, *Can. J. Chem.*, 51:3799–3807 (1973).

Paal, C., et al., Über katalytische wirkungen kolloidaler metalle der platingruppe. VIII. Die stufenweise reduktion der phenyl–propiolsäure, *Ber. Dtsch. Chem. Ges.*, 42:3930–39 (1909).

Pon, R.T., et al., Derivatization of controlled pore glass beads for solid phase oligonucleotide synthesis, *Biotechniques*, 6(8):768–770, 773–775 (1988).

Reese, C.B., et al., Oximate ion promoted unblocking of oligonucleotide phosphotriester intermediates, *Tetrahedron Lett.*, 2727–30 (1978). [missing volume].

Reese, C.B., The chemical synthesis of oligo– and poly–nucleotides by the phosphotriester aproach, *Tetrahedron*, 34:3143–79 (1978).

Rotermund, G.W., *Methoden der Orpanischen Chemie (Houben–Weyl)*, vol. IV/1b, Oxidation, part 2. Verlag, Georg Thieme, *Stuttgart*, pp. 176 (1975).

Scouten, W.H., et al., Reversible immobilization of antibodies on magnetic beads, *Analytical Biochemistry*, 205:313–318 (1992).

Shabarova, Z., et al., Table of contents, *Advanced Organic Chemistry of Nucleic Acids*, VCH Verlagsgesellschaft Weinheim, Germany (1994).

Sinha, N.D., et al., β–cyanoethyl N,N–dialkylamino/N–morpholinomonochloro phosphoamidites, new phosphitylating agents facilitating ease of deprotection and work–up of synthesized oligonucleotides, *Tetrahedron Lett.*, 24:5843–46 (1983).

Sinha, N.D., et al., Polymer support oligonucleotide synthesis XVIII[1,2]: use of β–cyanoethyl–N,N–dialkylamino–/N–morpholino phosphormidite of deoxynucleosides for the synthesis of DNA fragments simplifying deprotection and isolation of the final product, *Nucleic Acids Res.*, 12(11):4539–57 (1984).

Skita, A., et al., Reduktions Katalysen, *Ber. Dtsch. Chem. Ges.*, 43:3393–99 (1910).

Sonveaux, E., Reviews/The organic chemistry underlying DNA synthesis, *Bioorg. Chem.*, 14:274–325 (1986).

Stengele, K.P., et al., Improved synthesis of oligodeoxyribonucleotides, *Tetrahedron Lett.*, 31:2549–52 (1990).

Uhlmann, E., et al., Antisense oligonucleotides: A new therapeutic principle, *Chem. Rev.*, 90:543–84 (1990).

Uznanski, B., et al., Deoxyribonucleoside 3'–phosphordiamidites as substrates for solid supported synthesis of oligodeoxyribonucleotides and their phosphorothioate and DNA–triester analogues, *Tet. Lett.*, 28:3401–04 (1987).

van Boom, J.H., et al., Use of levulinic acid in the protection of oligonucleotides via the modified phosphotriester method: Synthesis of decaribonucleotide U–A–U–A–U–A–U–A–U–A, *Tetrahedron Lett.*, 4875–78 (1976). [missing volume].

Watkins, B.E., et al., Synthesis of oligodeoxyribonucleotides using N–benzyloxycarbonyl–blocked nucleosides, *J. Am. Chem. Soc.*, 104:5702–08 (1982).

Weiler, et al., High–loaded supports and the NPE/NPEOC–strategy: An efficient combination for large scale synthesis of oligonucleotides, *Solid Phase Synthesis & Combinatorial Libraries, Fourth International Symposium*, Sep. 12th–16th, 1995, Edinburgh, Scotland, Mayflower Scientific Limited, Birmingham, 1996 (Editor: Roger Epton).

Werstiuk, E.S., et al., Oligoribonucleotide synthesis. IV.[1] Approach to block synthesis, *Can. J. Chem.*, 50:1283–91 (1972).

Database WPI, Derwent Publication #7144464, citing German Patent No. 3644346.

Amarnath et al., "Chemical Synthesis of Oligonucleotides", *Chemical Reviews*, 77(2):183–217 (1977).

Caruthers et al., "Studies on Nucleotide Chemistry 15, Synthesis of Oligodeoxynucleotides Using Amidine Protected Nucleosides", *Nucleosides & Nucleotides*, 4(1&2):95–105 (1985).

Dreef–Tramp et al., "A New Protected Acyl Protecting Group for Exocyclic Amino Functions of Nucleobases", *Tetrahedron Letters*, 31(3):427–430 (1990).

Froehler et al., "Dialkylformamidlines: depurination resistant $N_6$–protecting group for deoxyadenosine", *Nucleic Acids Res*, 11(22):8031–8036 (1983).

Gioeli et al., "The Fluoren–9–ylmethoxycarbonyl Group for the Protection of Hydroxy–groups; Its Application in the Synthesis of an Octathymidylic Acid", *J Chem Soc Chem Commun*, pp. 672–674 (1982).

Hayakawa et al., "The Allylic Protection Method in Solid–Phase Oligonucleotide Synthesis. An Efficient Preparation of Solid–Anchored DNA Oligomers", *J Am Chem Soc*, 112:1691–1696 (1990).

Kamimura et al., "Diphenylcarbamoly and Propionyl Groups: A New Combination of Protecting Groups for the Guanine Residue", *Tetrahedron Letters*, 24(27):2775–2778 (1983).

Kharasch et al., "Derivatives of Sulfenic Acids. X. The Reaction of 2,4–Dinitrobenzenesulfenyl Chloride with Alcohols", *J Am Chem Soc*, 75:2658–2660 (1952).

Köster et al., "N–Acyl Protecting Groups for Deoxynucleosides", *Tetrahedron,* 37:363–369 (1981).

Letsinger et al., "Protecting Groups for Nucleosides Used in Synthesizing Oligonucleotides", *J Am Chem Soc,* 91(12):3356–3359 (1969).

McBride et al., "$N_6$ (N–Methyl–2–Pyrrolidine Amidine)Deoxyadenosine—A New Deoxynucleoside Protecting Group", *Tetrahedron Letters,* 24(29):2953–2956 (1983).

Ogilvie et al., "N–Levulination of Nucleosides", *Tetrahedron Letters,* 23(26):2615–2618 (1982).

Rasmussen et al., "The Synthesis of 3–(2'Deoxy–D–ribofuranosyl)adenine. Application of a New Protecting Group, Pivaloyloxymethyl (Pom)", *J Am Chem Soc,* 89(21):5439–5445 (1967).

Reese, C.B., *Tetrahedron Report No. 56,* "The Chemical Synthesis of Oligo– and Poly–Nucleotides by the Phosphotriester Approach", *Tetrahedron,* 34:3142–3179 (1978).

Sonveaux, E., "The Organic Chemistry Underlying DNA Synthesis", *Bioorganic Chem,* 14:274–325 (1986).

Ti et al., "Transient Protection: Efficient One–Flask Syntheses of Protected Deoxynucleosides", *J Am Chem Soc,* 104:1316–1319 (1982).

Vinogradov et al., "Synthesis and Physicochemical Studies of Partially Phosphate–Methylated Oligodeoxyribonucleotides", *Tetrahedron Letters,* 34(37):5899–5902 (1993).

Vu et al., "Fast Oligonucleotide Deprotection Phosphoramidite Chemistry for DNA Synthesis", *Tetrahedron Letters,* 50:7269–7272 (1990).

Watkins et al., "Symthesis of Oligodeoxyribonucleotides Using N–Benzyloxycarbonyl–Blocked Nucleosides", *J Am Chem,* 104:5702–5708 (1982).

COMBINATORIAL PROTECTING GROUP STRATEGY FOR MULTIFUNCTIONAL MOLECULES

This applications claims the benefit of Provisional Application No. 60/015,699 filed Apr. 17, 1996.

BACKGROUND OF THE INVENTION

Traditionally, drug development has not been based on genetic information. More rational approaches are currently possible, however, based on accumulated knowledge regarding the molecular mechanisms of infectious particles (viruses, bacteria, yeast, fungi and protozoa) and the target sites for antibiotics on the molecular level. Two new approaches which have promise for a more rational drug design are combinatorial chemistry (Gordon, E. M., et. al., *J. Med. Chem.*, 1994, 37, 1385–1401; Alper, J., *Science*, 1994, 264, 1399–1401) and antisense (Cohen, J. S., et al., *Scientific American international edition*, December 1994, pages 50–55).

In combinatorial chemistry, a large number of all variants of a specific family of compounds is synthesized and investigated for specific affinity to targeted modules i.e. receptor binding sites. The antisense approach utilizes suitably modified oligonucleotide sequences, which are designed to bind to essential regions for gene expression or virus or cellular replication resulting in complete suppression of the encoded functions.

H-phosphonate or phosphoramidite chemistries employing solid phase methods in automated DNA synthesizers are most efficient for the synthesis of oligonucleotides. The phosphoramidite method using B-cyanoethyl phosphoramidites as reactive nucleotide building blocks is the most prevalent synthesis method due to the quantitative condensation yields despite an oxidation step in every cycle (Sinha, N. D. et al., *Tetrahedron Lett.*, 1983, 24, 5843–46; Sinha, N. D. et al., *Nucleic Acids Res.*, 1984, 125 4539–57; Froehler, B. C. et al., *Nucleic Acids Res.*, 1984, 14, 5399–5407; Froehler, B. C. and Matteuci, M.D., *Tetrahedron Left*, 1986, 27, 469–72; Garegg, P. J. et at, *Tetrahedron Left*, 1986, 27, 4051–54; Sonveaux, E., *Bioorg. Chem.*, 1986, 14, 274–325; Uhimann, E. and Peyman, A., *Chem. Rev.*, 1990, 90, 543–84).

According to this method, DNA is synthesized typically in the 3'-5'-direction by using temporary acid labile 4,4'-dimethoxytrityl (DMTr) groups. The base (acyl amide bonds) and phosphate protection (β-cyanoethyl—deprotected via β-elimination) and the ester linkage to the support are cleaved in a single step by a nonselective reaction with concentrated aqueous ammonia.

To be useful as drugs, oligonucleotides must be able to penetrate through cell walls and nuclear membranes without undergoing enzymatic degradation. Unmodified oligonucleotides are generally unsuitable for this purpose. Therefore the development of modified oligonucleotides is essential for the antisense/triplex DNA approach. Various modifications have been introduced which mainly alter the internucleotide bond (i.e. methyl phosphonates, phosphorothioates and -dithioates, phosphate triesters, phosphoamidates, replacement of the internucleotide bond involving non-phosphorus containing moieties such as PNAs), the base, 2'-deoxyribose or linkage of various molecules at the 3'- or 5'-OH end of the oligonucleotide (Uhlmann, E. and Peyman, A., *Chem Rev.*, 1990, 90, 543–84; Nielsen, P. et. al., *Science*, 1991, 254, 1497; Beaucage, S. L. and Iyer, R. P., *Tetrahedron.*, 1993, 49, 6123; Nielsen, P. et. al., *Nucleic Acids Res.*, 1994, 22, 703–10).

Standard synthetic procedures typically result in depurination by the removal of the DMTr group in each elongation cycle (Shabarova, Z., Bogdanov, A. in *Advanced Organic Chemistry of Nucleic Acids*, VCH Verlagsgesellschaft Weinheim, Germany, 1994). In addition, since the synthesis usually is 3'-5'-directed. oligonucleotides substituted at their 3'-OH end are not easily available. Further, nonselective deprotection by ammonia is disadvantageous for the synthesis of modified DNA, if protecting groups are part of the modification strategy of oligonucleotides.

Antisense/triplex oligonucleotides have special requirements. The hybridization must be specific and strong enough to guarantee a sufficient blocking of mRNA or nuclear DNA target sequences. In addition, the oligonucleotides should be modified to protect against enzymatic degradation (e.g. by exo- and endonucleases) and to facilitate the passage through the cytoplasmic membrane (to access mRNA sequences) and the nuclear membrane (to target DNA sequences by forming triple helices). To be of therapeutic value, obviously, the modified oligonucleotides must also be non-toxic and the synthetic process must be amenable to easy and cost-effective upscaling.

Whether the target sequences of mRNAs are available for hybridization (i.e. located in loops or single stranded areas and not hidden in stem or tertiary structures) cannot be predicted with absolute certainty (Engels, J., *Natur. Chem. Techn. Lab.*, 1991, 39, 1250–54). In addition, a synthetic DNA may also bind to unexpected targets such as proteins (Cohen, J. S. et. al., *Scientific American, international edition*, December 1994, pages 50–55) as observed in tissue culture treated with phosphorothioate oligonucleotides. This could lead to further requirements and fine tuning for the modification, since improvements in one aspect may cause a disadvantage in another. For example the introduction of polycyclic aromatic compounds can lead to higher affinity for the complementary strand due to the intercalating properties but at the same time reduced specificity could result in an increased toxicity or mutagenicity (Engels, J., *Nachr, Chem. Techn. Lab.*, 1991, 39, 1250–54). In the triple helix approach there is a demand for special structures if the target sequences do not consist of a continuous stretch of purine residues which is a prerequisite for triple helix formation (Cohen, J. S., et. al., *Scientific American international edition*, December 1994, pages 50–55).

Progress in the syntheses of modified oligonucleotides is remarkable but only a few of the requirements can be fulfilled in one synthesis process since all available procedures lack versatility. Solid phase oligonucleotide synthesis using e.g. monomeric phosphodimorpholino amidites permits the creation of a variety of oligonucleotide phosphate triesters (Uznanski, B. et al., *Tetrahedron Lett.*, 1987, 28, 3401–04). However, the diversity of modification is limited to derivatizations of the phosphate moiety alone. In another example insertion of (R)- and (S)-3',4'-seco-thymidine in oligodeoxynucleotides (modification of the 2-deoxyribose) (Nielsen, P., et. al., *Nucleic Acids Res.*, 1994, 22, 703–10) resulted only in oligomers with good hybridization properties and stability against 3'-exonuclease degradation. All current synthetic methodologies and strategies are hampered by limited versatility and flexibility since the introduction of each modification requires a separate oligonucleotide synthesis run. The development of optimized modification schemes is therefore time consuming and costly.

There is a tremendous demand for synthetic strategies and methodologies which allow the generation of an almost unlimited amount of sequence specific modifications which can be obtained from one synthesis run. In addition, generation of combinatorial libraries of the same oligonucleotide sequence in various states of protection and/or modification allows the selection of molecules with affinities to non-nucleic acid molecules such as receptor sites by using the oligonucleotide backbone as an oligomeric scaffold exhibiting different patterns of functionalities available for specific molecular recognition processes.

SUMMARY OF THE INVENTION

The problems discussed above, which can be overcome by this invention, can be summarized as follows:

1) Using new protection schemes and solid phase synthesis, oligonuclectides are obtained in 5' to 3' direction using phosphoamidites and avoiding depurination. The 3'-OH protecting group employed is suitable as a purification handle for HPLC purification and can be detected in the visible spectral region with high sensitivity to determine condensation yields.

2) Each protecting group of the oligonucleotide (inclusive of the support-spacer moiety at the 5'- or 3'-OH end of the oligonucleotide) is removable selectively (multiselectivity of deprotection, principle of orthogonality). Furthermore, phosphate and base protecting groups can be removed and selected at preprogrammed positions. By substitution reactions, a simple and rapid synthesis of a variety of derivatives for the antisense/triplex concept can be made available. All possible derivatizations can be performed with only one oligonucleotide synthesis run. This versatile synthesis method is therefore amenable to scale-up.

3) Furthermore, the selective and orthogonal procedures and derivations can be applied to structures other than oligonucleotides. Thereby generating variously modified molecules to be tested for interactions with a specific molecular target or biological recognition process.

The above and further features and advantages of the instant invention will become clearer from the following Detailed Description and Claims.

DETAILED DESCRIPTION OF THE INVENTION

Figure 1:
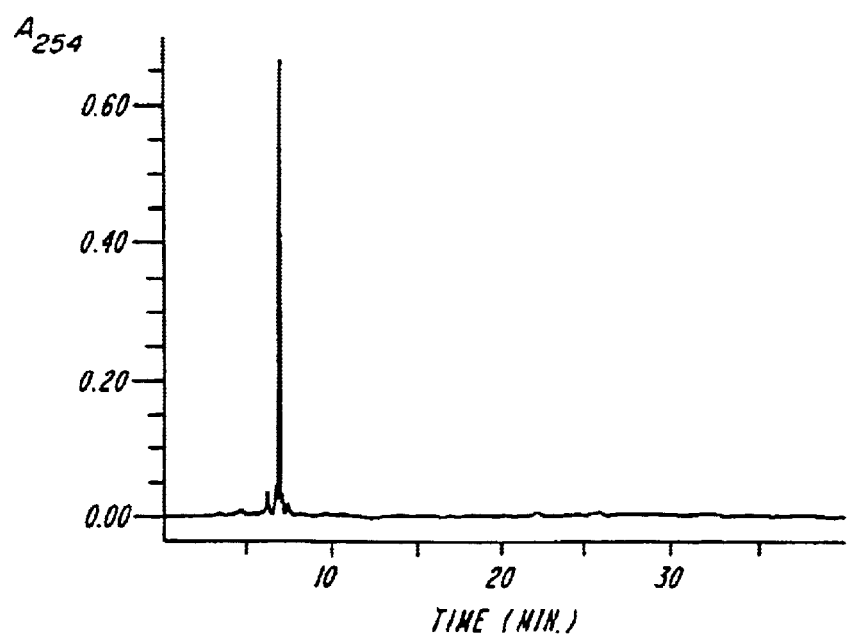
FIG. 1 is an HPLC chromatogram of a mixture of the oligodeoxynucleotide d(TAGCT) obtained by 5'-3' and 3'-5' directed syntheses.

As used herein, the following terms and phrases shall have the following meanings:

"monomer", or "building block" shall refer to a molecule with core structure M and plural reactive moieties that can be selectively protected or functionalized.

"oligomer", "oligomeric compound" or "polymer" refers to more than one covalently linked monomer or building block.

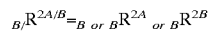

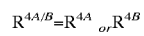

"npeoc/npe protection" means npeoc protection or npeoc and npe protection as shown in the description of scheme 1 for the npeoc/npe protected bases.

"Sequence specific derivations" means derivations at defined bases and/or phosphate moieties due to the different kind of base and phosphate protection group or ($R^{2A}$ or $R^{2B}$ and $R^{4A}$ or $R^{4B}$, respectively).

In general, the instant invention features new strategies for chemical polymer synthesis, which permit multiselective deprotection (for example via sequence dependent preprogrammed selection of appropriate nucleotide building blocks) to create polymers with predetermined modifications and/or functionalities. Various combinations of these specifically modified/functionalized monomers or oligomers can generate a combinatorial set of molecules available for specific molecular interaction or recognition experiments.

In certain embodiments herein, the syntheses are conducted on a solid support. Solid supports for use herein include beads, flat supports, wafers with or without pits and/or channels, the bottom of a microtiter plate or the inner walls of a capillary. Beads for use herein include polystyrene, polyamide, cellulose, agarose (e.g., SEPHAROSE®), dextran cross-linked with epichlorohydrin (e.g., SEPHADEX®), silica gel controlled pore glass (CPG), and polytetrafluoroethylene (e.g., TEFLON®).

The following scheme 1 presents a generalized 5' to 3' directed oligonucleotide synthesis resulting in oligomers for sequence specific selective and orthogonal deprotections and for subsequent derivatizations. The first step in the oligonucleotide synthesis cycle is the removal of $R^3$.

Scheme 1

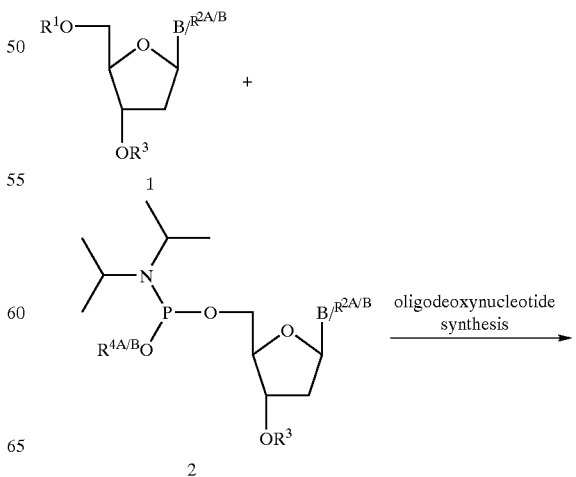

-continued

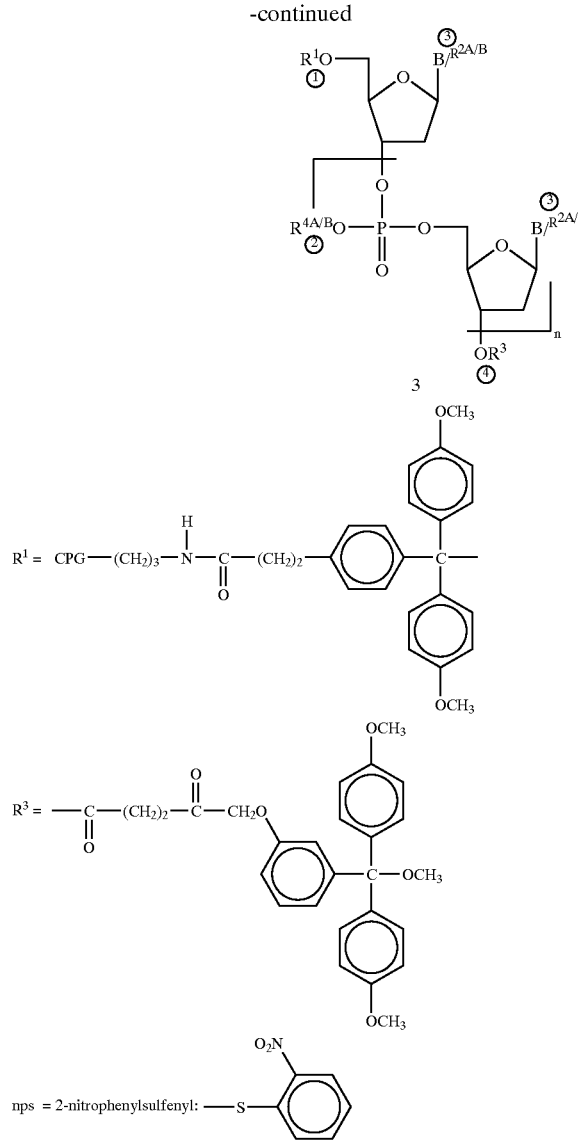

nps = 2-nitrophenylsulfenyl: —S—⟨⟩-NO₂

$B/R^{2A/B}$ = B or $B^{R^{2A}}$ or $B^{R^{2B}}$ $R^{4A/B}$ = $R^{4A}$ or $R^{4B}$ $R^{2A/B}$ = $R^{2A}$ or $R^{2B}$ $R^{4A}$ = β-cyanoethyl as protecting group for selective and orthogonal deprotection with reagent II (table 1), $R^{4B}$ = a protecting group stable with reagent II (table 1).

B = a natural or modified nucleobase, which does not require a protecting group during synthesis, $B^{R^{2A}}$, $B^{R^{2B}}$ = a natural or modified nucleobase with a protecting group, $R^{2A}$, $R^{2B}$ = different protecting groups, e.g. $R^{2A}$ is the nps protecting group in: $N^4$-nps-cytosine ($C^{nps}$), $N^6$-nps-adenine ($A^{nps}$), $N^2$-nps-guanine ($G^{nps}$) for selective and orthogonal deprotection according to table 1 and e.g. $R^{2B}$ is the npeoc,npe protection in: $N^4$-npeoc-cytosine ($C^{npeoc}$), $N^6$-npeoc-adenine ($A^{npeoc}$), $N^2$-npeoc-$O^6$-npe-guanine ($G^{npeoc,npe}$) stable under the deprotection conditions of table 1, npeoc = 2-(4-nitrophenyl)-ethoxycarbonyl, npe = 2-(4-nitrophenyl)-ethyl.

n: number of condensation reactions; ①, ②, ③, ④: protective positions;

CPG: Controlled-Pore-Glass.

As shown in scheme 1, a 2'-deoxyoligonucleotide, 3, is synthesized, e.g. by the phosphoramidite method (Sinha, N. D., Biernat, J., Köster, H. *Tetrahedron Lett.*, 1983, 24, 584346; Sinha, N. D., Biernat, J., McManus, J., Köster, H. *Nucleic Acids Res.*, 1984, 12, 4539–57; Sonveaux, E. *Bioorg. Chem.*, 1986, 14, 274–325). However, in contrast to the usual 3' to 5' addition, the synthesis is performed in the 5' to 3' direction using the building blocks 1 and 2. During an elongation cycle, the temporary protecting group, $R^3$, is removed, e.g. using a neutral hydrazine reagent IV (table 1) before the condensation step and the acidified filtrate of the hydrazinolysis solution is spectrophotometrically measured to determine the preceding condensation yield. In this manner, a trityl assay as typically used with the 4, 4'-dimethoxytrityl group, is possible. In addition, there is little risk of depurination, since acidic conditions are not used during the synthesis cycles.

Selective and orthogonal deprotections are possible if at the linkages ①–④ of oligomer 3, deprotections are selectively done as shown in the following table 1.

TABLE 1

Selective and orthogonal deprotection at oligomer 3.

| Deprotection at linkage in 3 | Reaction | Deprotection reagent |
|---|---|---|
| ① | detritylation | I: 80% acetic acid |
| ② | decyanoethylation | II: tertbutyl amine/ pyridine 1/9 (v/v) |
| ③ | base deprotection | III: p-thiocresole in pyridine/DMF 3/7 (v/v): 3 mmol/ml |
| ④ | hydrazinolysis | IVa: 1 M hydrazinium hydrate in pyridine/glacial acetic acid/ water (4:3:0.35, v/v), pH 5.4 |
| | | IVb: 0.5 M hydrazinium hydrate in pyridine/glacial acetic acid/ water (4:1:0.25, v/v), pH 6.5 |

Selective deprotections allow the following 16 deprotection combinations: fully protected oligomer, fully deprotected oligomer ((①, ②, ③, ④) or partially deprotected oligomers after the following combinations of deprotection reactions, deprotected at positions: (①, ①+②, ①+②+③, ①+③, ①+④, ①+③+④, ①②+④, ②, ③, ④②, +③, ②, +④, ③, +④, ②+③+④)). Within the combinations of deprotection reactions, the order of deprotection can be chosen. In addition, the use of differently base and/or phosphorus protected building blocks 1 and 2 (scheme 1) during the oligonucleotide synthesis furnishes sequences with base and/or phosphate specific open functionalities. After each deprotection, the nucleophilic group of the oligomer can be reacted with a new substituent or can remain unprotected. Only a minimal quantity of support is needed to create such a newly derivatized oligomer, so that a large variety of derivatizations is possible with just one oligomer synthesis run. New substituents can be introduced into the immobilized oligonucleotide by the reaction of an excess of the appropriate reagents in their reactive forms (e.g. acyl chlorides, anhydrides), in case of the phosphate group in presence of condensing agents (e.g. aromatic sulfonyl chlorides or derivatives thereof) (Heikklia, J., Balgobin, N Chattopadhyaya, J. *Acta Chem. Scand.*, 1983, B37, 857–62; Köster. H. *Nachr. Chem. Techn. Lab.*, 1979, 27, 694–700). Any excess of the reagent can then be removed, e.g. by filtration. The simplicity of these substitutions can be compared with the "capping"—step in DNA synthesis and in principle can be performed on an automated DNA synthesizer.

Scheme 2 shows an example of an immobilized fully protected oligomer 3 for sequence specific derivatizations by the use of differently base and/or phosphorus protected building blocks 1 and 2 of scheme 1 using the reagents of table 1.

Scheme 2

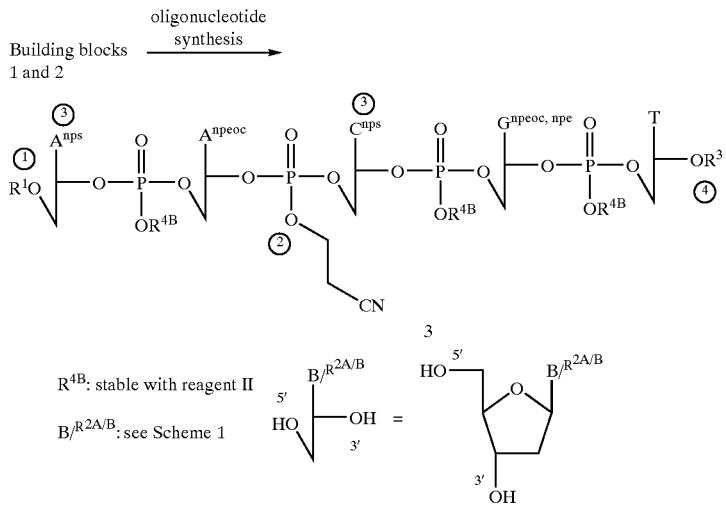

The selective and orthogonal deprotections and the derivatizations by introducing new substituents can be carried out at positions ①–④, at ② and ③, in a sequence specific way. During the derivatizations at ①–④ only the npeoc/npe base protection remains intact. In contrast, the phosphate protecting group $R^{4B}$ needs to remain intact if derivatizations at ② are to be performed. These two protecting groups only serve to carry out sequence specific derivatizations at ② and/or ③. After the derivatizations at least the bases, protected with npeoc/npe groups have to be deprotected without removing new substituents at at the ①–④ same time. The removal of the npeoc/npe groups is necessary to guarantee sufficient hybridization properties of the derivatized oligomers with complementary nucleic acid sequences.

Base Protection

The npeoc/npe protection was found to be stable during deprotection conditions of compound 3 at position ①–④ (scheme 1 and 2) with the reagents I–IV (table 1). During the npeoc/npe deprotection with DBU reagent, no removal of the new substituents at ①–④ is desired. These new substituents are linked for example at positions ① and ④ via (trityl) ether or carbonic acid ester bonds e.g., at ② via phosphate ester bonds e.g., at ③ via amide bonds to the oligomer. The stability of phosphate ester, carbonic acid ester and the nucleoside base amide bond during npeoc/npe deprotection has been described (Stengele, K. P., Pfleiderer, W., *Tetrahedron Lett.*, 1990, 31, 2549–52; Himmelsbach, F., Schulz, B. S. Trichtinger, T., Ramamurthy, C., Pfleiderer, W., *Tetrahedron.* 1984, 40, 59–72). These deprotection conditions were found not to affect the trityl ether bond and the nps base protection. Other base protecting groups, in addition to the npeoc/npe protection, should be suitable for use in the process of the invention.

Phosphate Protection

The stability of $R^{4B}$ during the deprotections at ①, ③ and ④ is not absolutely necessary. If $R^{4B}$ is removed, e.g. during deprotection at position ④ using reagent IV, reaction of the OH group at position ④ with an acyl chloride would result in a mixed anhydride at the phosphate moiety, which subsequently could be either transformed to a newly protected function or hydrolyzed to the phosphodiester. Of course, the substitution at position ② should be carried out before; $R^{4B}$ must be stable with reagent II, to guarantee a sequence specific derivatization at position ②.

The phosphate protection with the p-chlorophenyl group e.g. is stable with reagent II in contrast to the β-cyanoethyl group (Hsiung, H. M., *Tetrahedron Lett.*, 1982, 23, 5119–22). The phosphate protection with the o-chlorophenyl group e.g. is stable with 0.5M hydrazine reagent (Watkins, B. E., Kiely, J. S., Rapoport, H., *J. Am. Chem. Soc.*, 1982, 104, 5702–08). The phosphate protection with the 2,5-dichlorophenyl group e.g. is stable with strong acids as p-toluenesulfonic acid in methylene chloride/methanol (Himmelsbach, F., Schulz, B. S., Trichtinger. T., Ramamurthy, C., Pfleiderer, W., *Tetrahedron*, 1984, 40, 59–72). During the deprotection of $R^{4B}$ no removal of the new substituents at ①–④ is desired. The o-chlorophenyl group e.g. allows deprotection with 4-nitrobenzaldoximate without affecting benzoic acid ester and nps amide bonds (Heikkilä, J., Balgobin, N., Chattopadhyaya, J., *Acta Chem. Scand.*, 1983, B37, 857–62). Further the o-chlorophenyl group e.g. is easily removable with (n-butyl)$_4$NF (Reese, C. B., Titmas, R. C., Yau, L., *Tetrahedron Lett.*, 1978, 2727–30). Under these conditions acetic acid ester, trityl ether bonds and the nucleoside base protection with the acetyl or benzoyl groups remain intact (Ogilvie, K. K., *Can J. Chem.*, 1973, 51, 3799–3807).

In addition to the described 16 deprotection combinations at positions ①–④ selective and orthogonal deprotections at the different nps protected bases (e.g. deprotection at $C^{nps}$ before $A^{nps}$ in oligomer 3, schemes 1 and 2) could lead to a maximum of 64 deprotection combinations. The rate of base deprotection in nps base protected nucleosides was found to be significantly influenced by the deprotection reagent (thiocresolate concentration and solvents). The rate of deprotection in 0.02M thiocresolate in pyridine decreases as follows: 2'-deoxy-$N^2$-nps-guanosine ($G_d^{nps}$)>>2'-deoxy-$N^4$-nps-cytidine ($C_d^{nps}$)>>2'-deoxy-$N^6$-nps-adenosine ($A_d^{nps}$). It would seem to be difficult to identify reagents leading to a reversion of this order to obtain e.g. nps protected cytosine and guanine in the presence of nps deprotected adenine moieties. But such a deprotection state could be achieved by selective deprotection of the $C^{nps}$ and $G^{nps}$ moieties, followed by reprotecting them with groups, stable with thiocresolate reagent. Finally $A^{nps}$ can be deprotected with this reagent. In yet another approach, this protection scheme can be obtained by using the suitably protected nucleotide building blocks during oligomer synthesis.

Compared to current oligodeoxynucleotide syntheses for use in antisense and triplex DNA therapies (Cohen, J. S., Hogan, M. E., *Scientific American, Int. Ed.*, December 1994, pages 50–5514; Uhlmann, E., Peyman, A., *Chem Rev.*, 1990, 90, 543–84; Beaucage, S. L., Iyar, r. P. Tetrahedron, 1993, 49, 6123–94), the new strategy shows a remarkable advantage. All possible derivatizations can be performed with only one oligonucleotide synthesis run.

The strategy presented above, can be modified according to other oligonucleotide synthesis schemes. For example, in addition to the phosphoramidite method shown in scheme 1, the strategy can be employed with the phosphotriester and other suitable methods of oligonucleotide synthesis. For the phosphotriester method, chloro substituted phenyl groups and the β-cyanoethyl group were successfully used as phosphate protection groups (Amarnath, V., Broom, A. D. *Chem. Rev.* 1977, 77, 183–217; Reese, C. B., *Tetrahedron*, 1978, 34, 3143–79). The levulinic acid ester and the npeoc/npe base protection are stable during the reaction conditions of the phosphotriester method (Himmeisbach, F., Schulz, B. S., Trichtinger, T., Ramamurthy, C., Pfieiderer, W., *Tetrahedron*, 1984, 40, 59–72; van Boom, J. H., Burgers, P. M. J., Tetrahedron Lett., 1976, 4875–78). The nps base protection has been successfully used during the oligonucleotide synthesis by the phosphotriester approach (Heikkila, J., Balgobin, N., Chattopadhyaya. J., *Acad Chem. Sci.*, 1983, B37, 857–62). The structure of oligomers obtained in this way of synthesis is the same as for the oligomer 3 generated by the phosphoramidite method (scheme 1). For syntheses by the phosphoramidite method, amidites, whose 5'-OH or 3-OH groups respectively are protected with the 4,4'-dimethoxytrityl (DMTR) group, are used. Scheme shows a general view and scheme 4 to 6 show specific examples.

Scheme 3

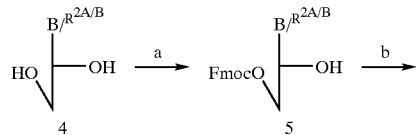

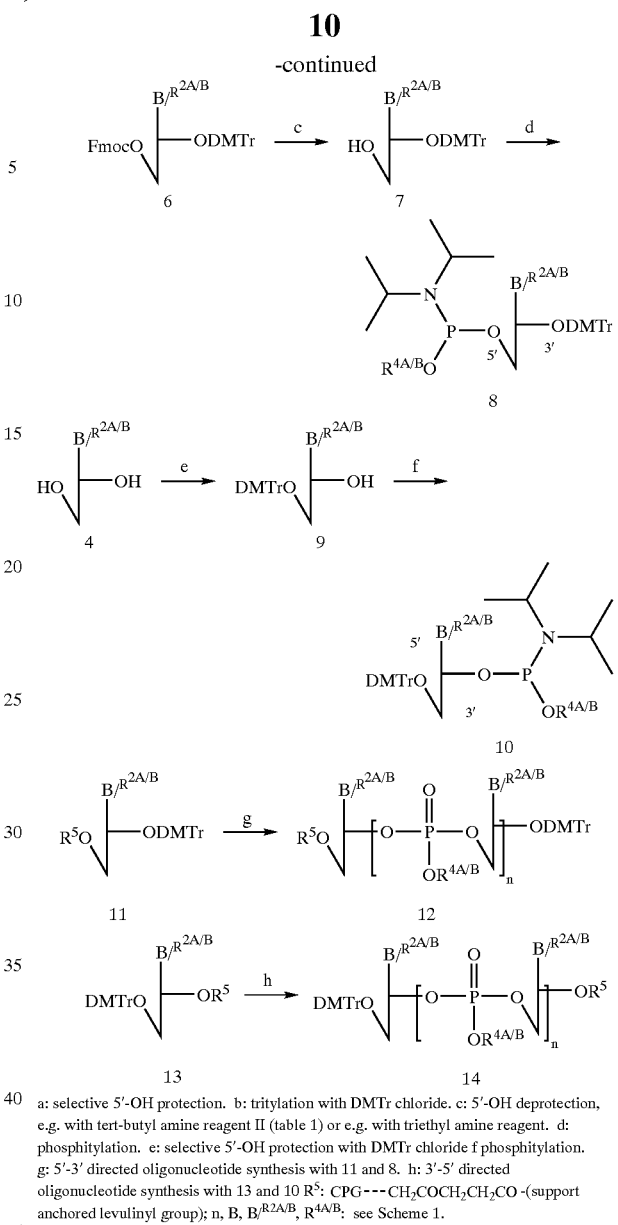

a: selective 5'-OH protection. b: tritylation with DMTr chloride. c: 5'-OH deprotection, e.g. with tert-butyl amine reagent II (table 1) or e.g. with triethyl amine reagent. d: phosphitylation. e: selective 5'-OH protection with DMTr chloride f phosphitylation. g: 5'-3' directed oligonucleotide synthesis with 11 and 8. h: 3'-5' directed oligonucleotide synthesis with 13 and 10 $R^5$: CPG---$CH_2COCH_2CH_2CO$ -(support anchored levulinyl group); n, B, $B/R^{2A/B}$, $R^{4A/B}$: see Scheme 1.

Scheme 4

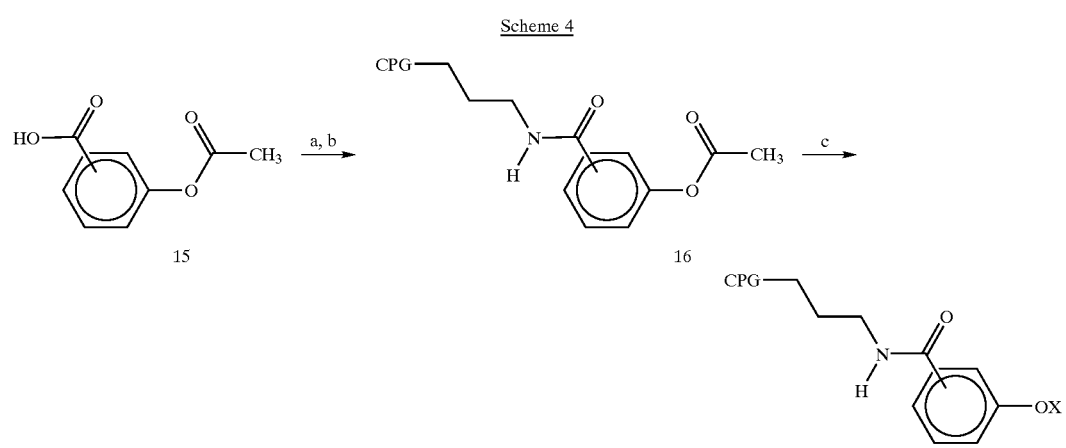

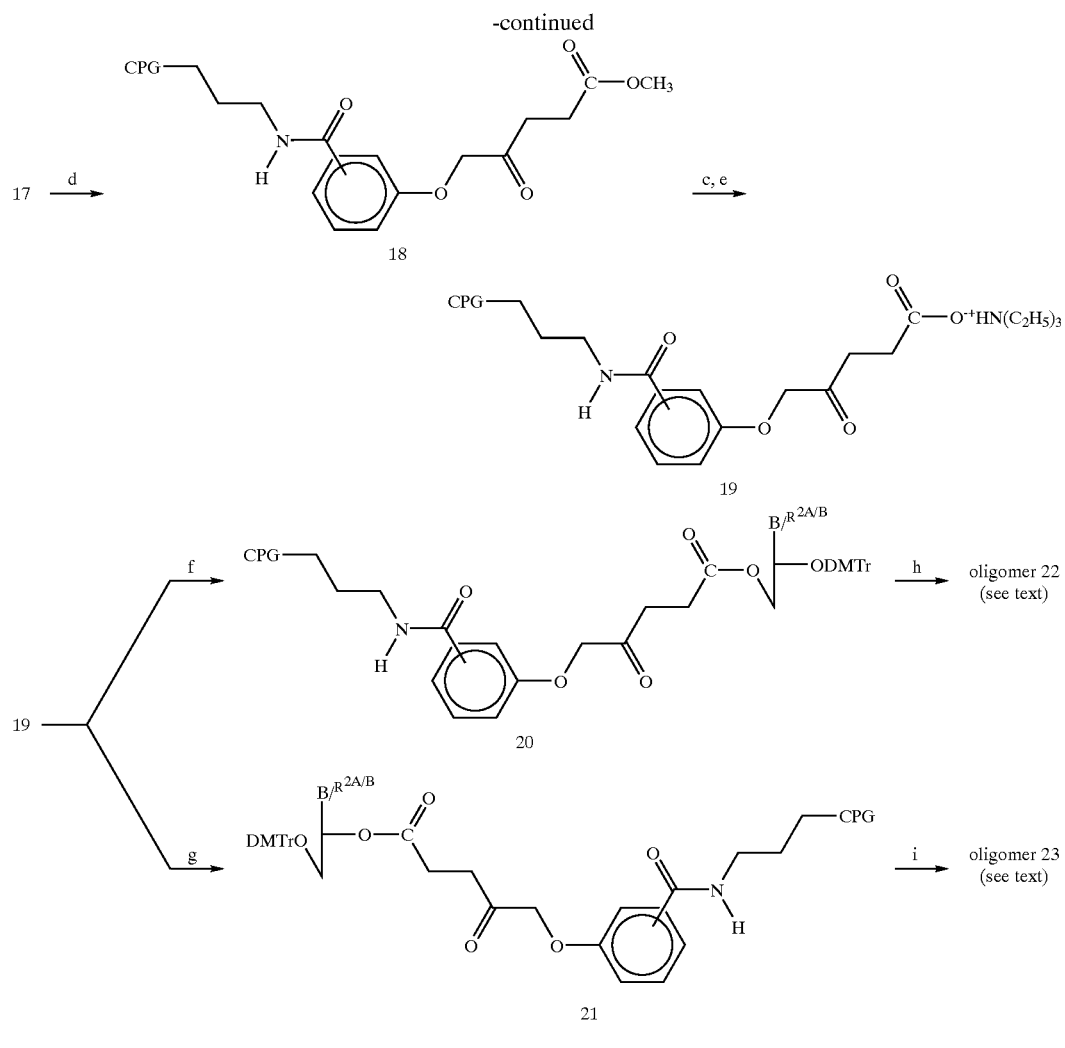

Description of Scheme 4:

aromatic substitution: ortho, meta or para a: formation of acid anhydride with DCC. b: aminolysis of the formed anhydride with aminopropyl CPG. c: saponification with 32% ammonia solution (X=NH$_4^+$) or K$_2$CO$_3$/methanol/water (ratio: 6.95 g/87.4 ml/69.5 ml; X=K$^+$)[1]. d: reaction with 5-bromo-levulinic acid methyl ester in DMF[2]. e: protonation with 2% KHSO$_4$ solution, deprotonation with triethyl amine. f,g: reaction with compound 7 or 9 (scheme 3) respectively in ethylene dichloride e.g. with DCC[3] capping of unreacted carboxyl functionalities with methanol (Gupta, K. C. et al., *Nucleic Acids Res.*, 1991, 19, 3019–25). h, i: oligonucleotide synthesis with amidite 8 or 10 (scheme 3) respectively to the oligomers 22 or 23 (fully protected oligomers). Remarks: 1) Washing to remove alkaline solution 2) washing to remove NH$_4$Br or KBr, other washing steps are not listed 3) or reaction of the imidazolide of compound 19 e.g. with compound 7 or 9 (scheme 3).

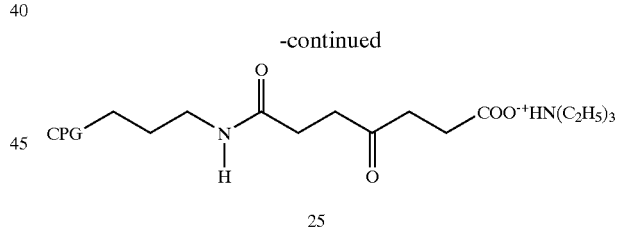

a: formation of acid anhydride of 24; aminolysis with e.g. : 2.2mmol of compound 24, 0.43 mmol DCC, 0.02 mmol 4-dimethylaminopyridine in 4 ml dioxane/triethyl amine 9/3 (v/v) and 1 g aminopropyl CPG; capping reaction with 0.33 ml acetic anhydride; washing with dioxane, methanol, DMF and water. b: reaction with K$_2$CO$_3$/methanol/water (ration: see scheme 4), washing with water. c: protonation with 2% KHSO$_4$ solution, washing with water, ethanol and ether. d: reaction with triethyl amine to compound 25, washing with ethylene dichloride. Further steps correspond to the steps f–i of scheme 4.

Scheme 5

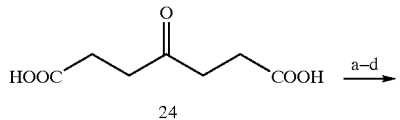

Scheme 6

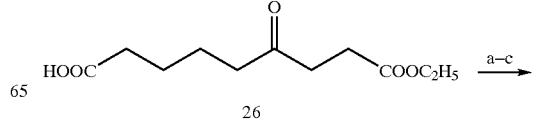

-continued

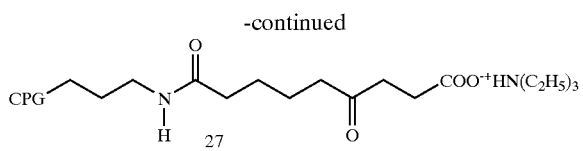

27 a: reaction of 26 (Johnson, W.S. and Hunt, R.H., *J Amer. Chem. Soc.*, 1950, 72, 935–39) with DCC e.g. to the acid anhydride. b: aminolysis with aminopropyl CPG. c: saponification, protonation with 2% KHSO$_4$ solution, deprotonation with triethyl amine. Further steps correspond to the steps f–i of scheme 4.

Based on the schemes presented above, one of skill in the art can modify schemes to accommodate phosphotriester and other suitable methods to generate a combinatorial set of protected molecules having a plurality of moieties, wherein each moiety can be individually deprotected and subsequently derivatized. It is intended that all such modifications fall within the scope of the instant invention.

The following findings demonstrate the feasibility of this extension of the synthetic strategy with the levulinic acid ester bridge. The base protection of nucleosides protected with the 2-nitrophenylsulfenyl (nps) group is rather stable with strongly acidic solutions (Heikkila, J., Balgobin, N., Chattopadhyaya, J., *Acta Chem. Scand.*, 1983, B37, 857–62). We found that stability against depurination in 80% acetic acid decreases as follows: 2'deoxy-N$^6$-nps-adenosine ($A_d^{nps}$)>>2'-deoxy-N$^2$-nps-guanosine ($G_d^{nps}$)>2'-deoxy-N$^2$isobutyryl-guanosine ($G_d^{ib}$)>>2'-deoxy-N$^6$-benzoyl-adenosine ($A_d^{bz}$); $G_d^{ib}$ and $A_d^{bz}$ are exposed to strong acids in every elongation cycle in the standard DNA synthesis process (Sinha, N. D., Biernat, J., Köster, H., *Tetrahedron Lett.*, 1983, 24, 5843–46; Sinha, N. D., Biernat, J., McManus, J., Köster, H., *Nucleic Acids Res.*, 1984, 12, 4539–57; Sonveaux, E., *Bioorg. Chem.*, 1986 14, 274–325). In accordance with Heikkilä, J. et. al. (*Acta Chem. Scand.*, 1983, B37, 857–62), $A_d^{nps}$ does not depurinate with 80% acetic acid, although the main depurination problem in standard DNA synthesis is caused by the $A_d^{bz}$ units. 2'-Deoxy-N$^4$-nps-cytidine ($C_d^{nps}$) is stable with 80% acetic acid. No problem caused by depurination is observed with npeoc/npe base protection (Stengele, K. P., Pfleiderer, W., *Tetrahedron Lett.*, 1990, 31, 2549–52).

To test the new strategy d(TAGCT) and d(TTTT) were synthesized by a 5'-3' directed DNA synthesis with support 1 (scheme 1, $_B/R^{2A/B}$=thymine) and amidites 2 (scheme 1, $_B/R^{2A/B}$=thymine, npeoc/npe protected bases, $R^{4A/B}$=β-cyanoethyl, corresponding to 2a–d of scheme 7). The 3'-OH protection was removed with hydrazine reagent IV (table 1) at near neutral pH, forming a heterocyclic compound which is detected in the visible spectral region with high sensitivity after being acidified (Leikauf, E., Köster, H., *Tetrahedron*, 1995, 51, 5557–62. To obtain the desired high condensation yields, addition of the amidite solution had to be preceded by the activation with tetrazole. The oligomer could be removed from the support by a short treatment with 80% acetic acid without affecting the 3'-OH protection. Suitability of the 3'-OH protection group as "purification handle" (Sinha, N. D., Biernat, J., Köster, H., *Tetrahedron Lett.*, 1983, 24, 5843–46; Sinha, N. D. Biernat, J., Köster, H., *Nucleic Acids Res.*, 1984, 12, 4539–57; Sonveaux, B., *Bioorg. Chem.*, 1986, 14, 274–325) is comparable with the DMTr group. Removal of the β-cyanoethyl group was carried out after synthesis of the protected d(TTTT) with tert-butyl amine reagent (table 1), after synthesis of the protected d(TAGCT) with 0.5M DBU in acetonitrile (Stengele, K. P., Pfleiderer, W., *Tetrahedron Lett.*, 1990, 31, 2549–52) (together with the removal of the base and the 3'-OH protection). Because of the lability of the 3'-OH protection with DBU reagent, the levulinyl group should be substituted by an acyl group stable with DBU reagent before removing the oligomer from the support, if maintaining of the purification handle effect is desired. The 3-{4-[bis-(4-methoxyphenyl)-methyl]-phenyl}-propionyl group of compound 36 (scheme 8), the triphenylmethoxyacetyl (Werstiuk, E. S., Neilson, T., *Can. J. Chem.*, 1972, 50, 1283–91) or the diphenyl-tert-butyl silyl group (Köster, H., Biernat, J, McManus, J., Sinha, N. D., 1985, *Natural Products Chemistry*, could be such an acyl group. Further experimental steps were similar to the 3'-5' directed DNA synthesis (Sinha, N. D., Biernat, J., Köster, H., *Tetrahedron Lett.*, 1983, 24, 5843–46; Sinha, N. D., Biernat, J., McManus, J., Köster, H., *Nucleic Acids Res.*, 1984, 12, 4539–57; Sonveaux, E., *Bioorg. Chem.*, 1986, 14, 274–325).

Figure 2:
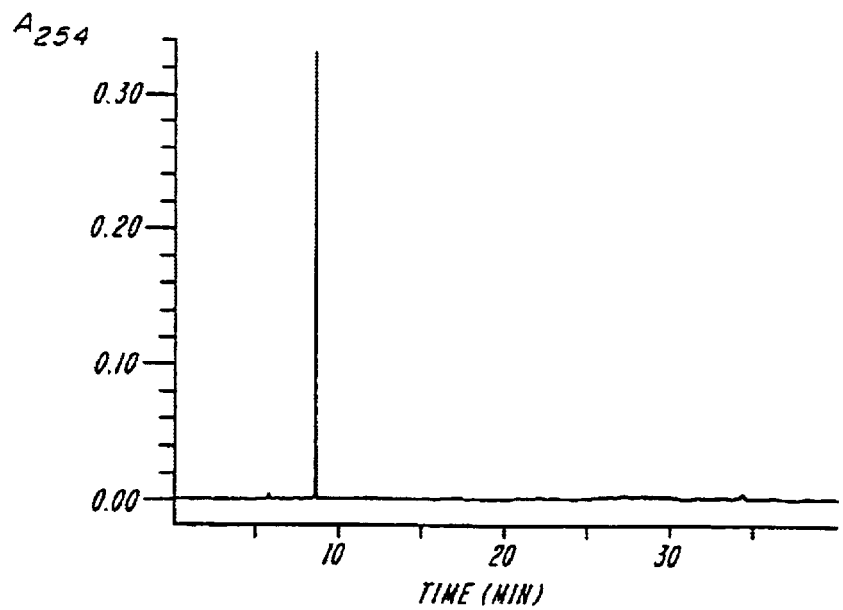
FIG. 2 is an HPLC chromatogram of a mixture of the oligodeoxynudeotide d(TTTT) obtained by 5'-3' and 3'-5' directed syntheses.
Figure 3:
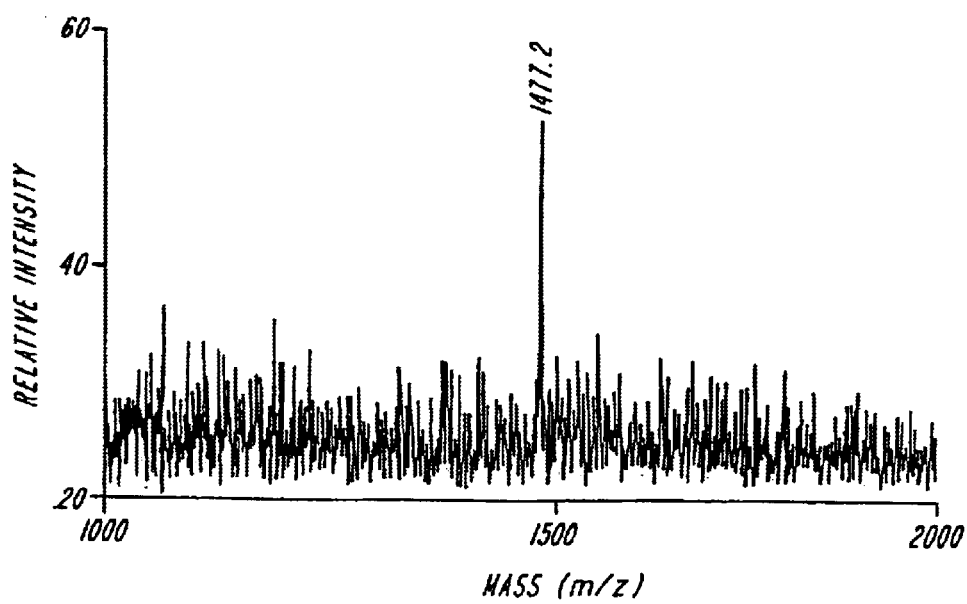
FIG. 3 is a MALDI-TOF mass spectrum of the oligodeoxynucleotide d(TAGCT) obtained by 5'-3' directed synthesis.
Figure 4:
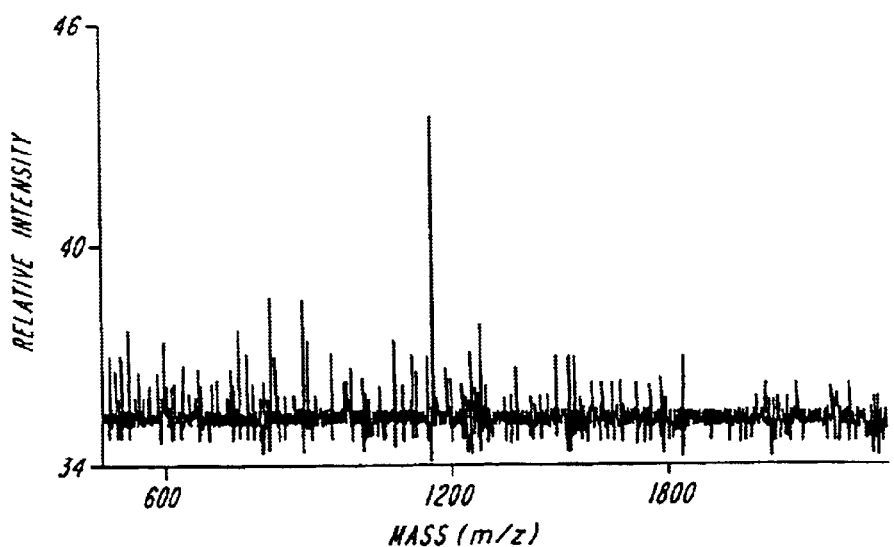
FIG. 4 is a MALDI-TOF mass spectrum of the oligodeoxynucleotide d(TTTT) obtained by 5'-3' directed synthesis.
Figure 5:
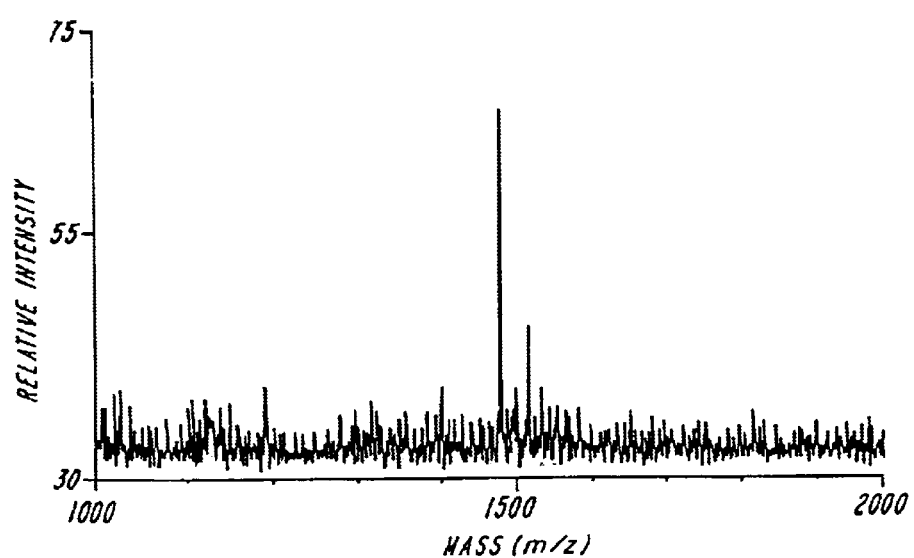
FIG. 5 is a MALDI-TOF mass spectrum of the oligodeoxynucleotide d(TAGCT) obtained by 3'-5' directed synthesis.

To demonstrate identity of the synthesized oligomers following the different synthetic routes (3'-5' versus 5'-3' direction) the oligomers were fully deprotected and analyzed by HPLC. Simultaneous analyses of either the two d(TAGCT) or d(TTTT) oligomers resulted in one single peak, proving identity (FIGS. 1 and 2). The fully deprotected oligomers d(TAGCT) and d(TTTT) were further characterized by MALDI-TOF mass spectra (FIGS. 3 and 4). In FIG. 5 a spectrum of d(TAGCT) obtained by the 3'-5' directed synthesis is shown.

The immobilized fully protected d(TTTT) (oligomer 3, $_B/R^{2A/B}$=thymine, $R^{4A/B}$=β-cyanoethyl) already exhibited eight different combinations of deprotection with the reagents I, II, IV of table 1. To demonstrate the orthogonal deprotection (16 deprotection combinations) for the fully protected mixed oligomer 3 of scheme 1 (for the bases A, G, C the protecting group $R^{2A/B}$=$R^{2A}$=nps, $R^{4A/B}$=$R^{4A}$=β-cyanoethyl) with the optimized deprotection reagents I–IV of table 1, additional deprotection experiments were carried out with the immobilized oligomers 5'-O—R$^1$-d(TTTT)-3'-O—R$^3$, 5'-O—R$^1$-d(TAGCT)-3'-O—R$^3$ (R$^1$, R$^3$ as in scheme 1) and in solution with the model compounds 5'-O-DMTr-2'-deoxythymidine [(DMTr)T$_d$], 28, 29a, 30a (scheme 10), $G_d^{nps}$, $A_d^{nps}$, $C_d^{nps}$. The deprotection reagents removed one protecting group quickly, while the other groups were stable under these conditions for at least 24 h. This is demonstrated by the following results: 1) reagent I (80% acetic acid): the 3'-O-protected d(TTTT) and d(TAGCT) are removed from the support after 15 minutes by detritylation, in compound 28 only the DMTr group is cleaved, compound 30a is only transformed to compound 29a which is stable, the nps groups of the nps protected nucleosides are not removed (only at $G_d^{nps}$ depurination is observed, but slower compared to $G_d^{ib}$); 2) reagent II (tert-butyl amine reagent): decyanoethylation is complete with compound 28 after 40 minutes, (DMTr)T$_d$, compounds 29a, 30a and the nps protected nucleosides are stable; 3) reagent III (thiocresolate reagent): nps groups are removed at $G_d^{nps}$, $C_d^{nps}$ after 5 minutes, at $A_d^{nps}$ after 45–60 minutes, compounds 28, 29a, 30a are stable; 4) reagents IVa, IVb (hydrazine reagents): delevulination is complete with compounds 29a and 30a after 8 minutes, compound 28 and the nps protected nucleosides are stable.

$G_d^{nps}$, $A_d^{nps}$ and $C_d^{nps}$ are not affected by 0.02M iodine reagent which is used for oxidation reaction during oligodeoxynucleotide synthesis. Experiments for base specific deprotections: $G_d^{nps}$, $C_d^{nps}$ are stable with 0.5M DBU in acetonitrile for 24 h, $A_d^{nps}$ only shows a slight deprotection after this time. Compounds 30b–d were stable with reagents II and III for at least 24 h, the stability of the npeoc/npe base protection with reagents I and IV is demonstrated e.g. by the synthesis of the oligomer d(TAGCT).

The following Scheme 7 shows the synthesis of the building block 2 used for the oligonucleotide synthesis of scheme 1 and 2; and Scheme 8 shows the synthesis of the building block 1 used for the oligonucleotide synthesis of scheme 1 and 2.

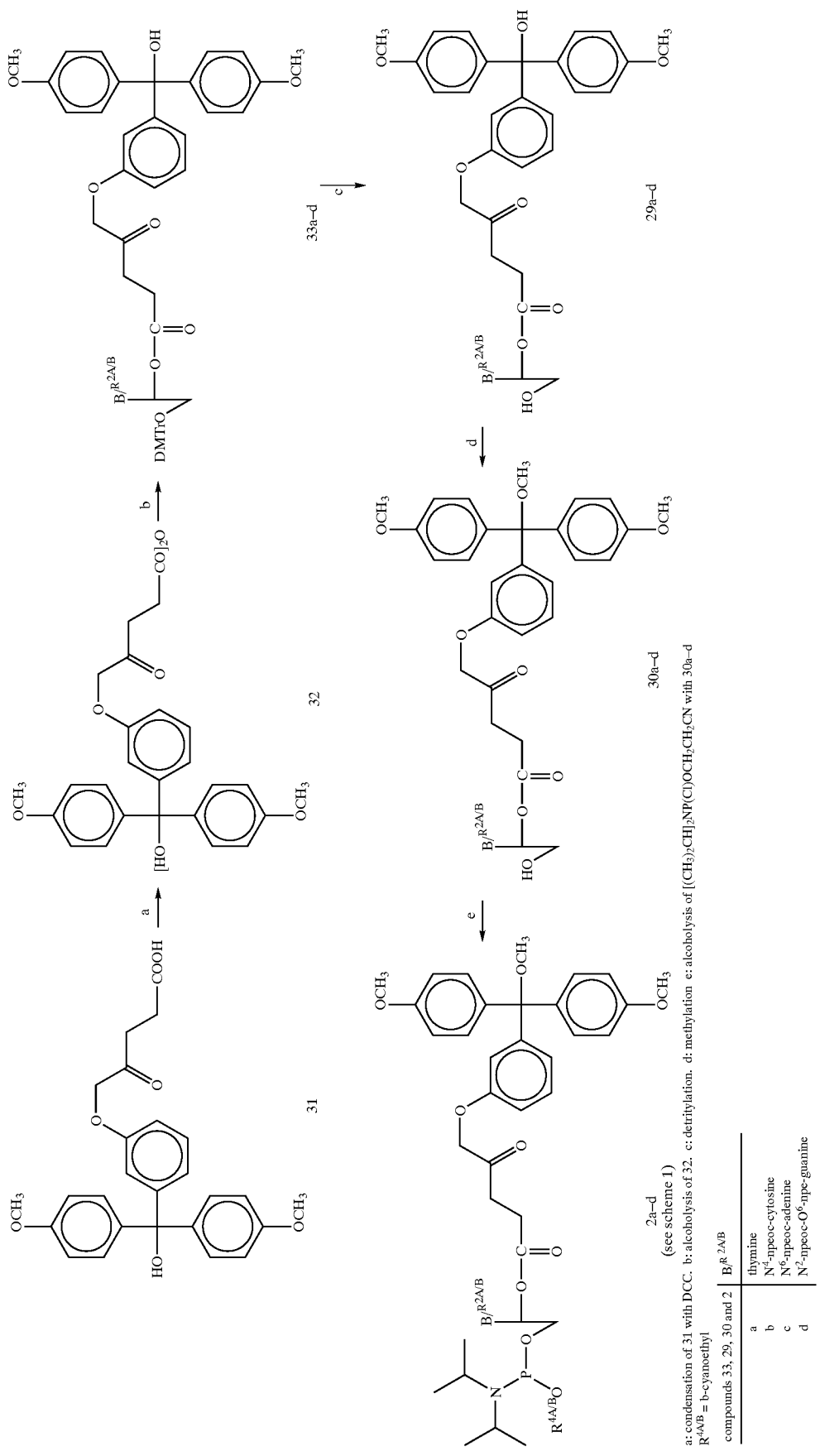

Scheme 8

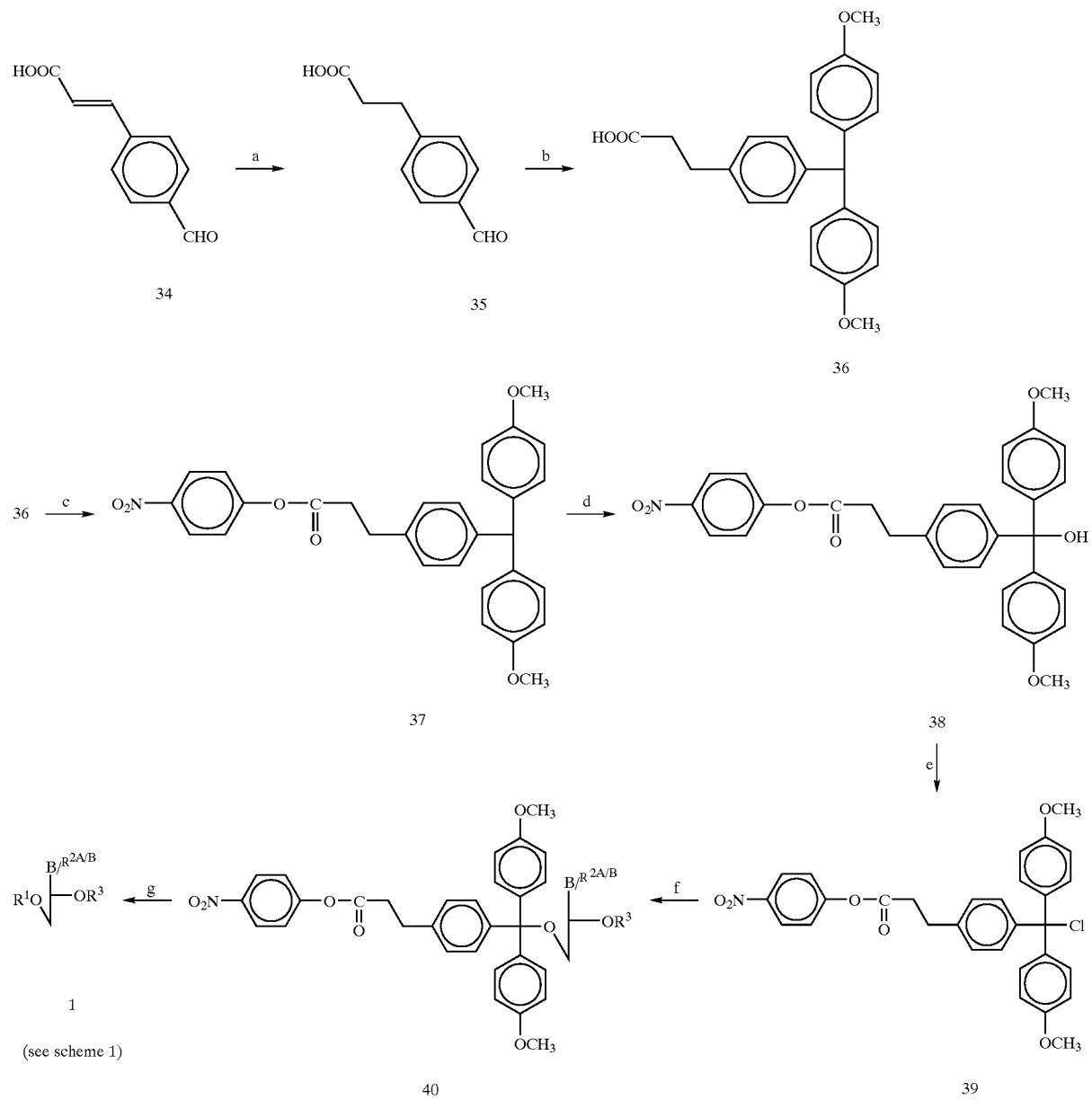

a: hydrogenation. b: electrophilic aromatic substitution with anisole. c: esterification. d: oxidation. e: chlorination of 38. f: alcoholysis with 30a (scheme 7, $_B/R^{2A/B}$: thymine). g: aminolysis with aminopropyl CPG to compound 1 ($R^1$, $R^3$: see Scheme 1).

Another embodiment of the invention employs the combinatorial protecting group strategy with other multifunctional molecules. The oligomer 3 of scheme 1 has four protected moieties, suitable for selective and orthogonal deprotection with the reagents I–IV (table 1): 1) the β-cyanoethyl protected phosphate moiety, 2) the tritylether moiety, 3) nps protected amino groups and 4) the levulinic acid ester moiety.

Selective and orthogonal deprotections is possible with multifunctional molecules whose core structure M (scheme 9) is different to the structure of oligomer 3 (i.e. low molecular weight multifunctional molecules or biomolecules such as peptides, lipids and oligosaccharides). Use of the process of the invention facilitates creation of a high number of derivatives for combinatorial experiments (Gordon, B. M., Barrett, R. W., Dower, W. J., Fodor, S. P. A., Gallop, M. A., *J. Med. Chem.*, 1994, 37, 1385–1401; Alper, J., *Science*. 1994, 264, 1399–1401). Multifunctional molecules need not be limited by the presence of phosphate, OH and amino functionalities (as in oligonucleotides) but could contain only OH functionalities or other combinations of functional groups. The Fmoc group in the 5'-O-Fmoc-2'-deoxythymidine (Gioeli, C., Chattopadhyaya, J. B.,*J. Chem. Soc. Chem. Commun.*, 1982, 672–74) showed orthogonal deprotection properties with I–IV (table 1) and the 2,4-dinitrophenylsulfenyl (dnps) group in the dnps ethyl ester (Kharasch, N., McQuarrie, D. P., Buess, C. M., *J. Amer. Chem. Soc.*, 1953, 75, 2658–60) reveals comparable selective deprotection properties with reagents I–IVa to the 2-nitrophenylsulfenyl (nps) group in the nps amide moiety.

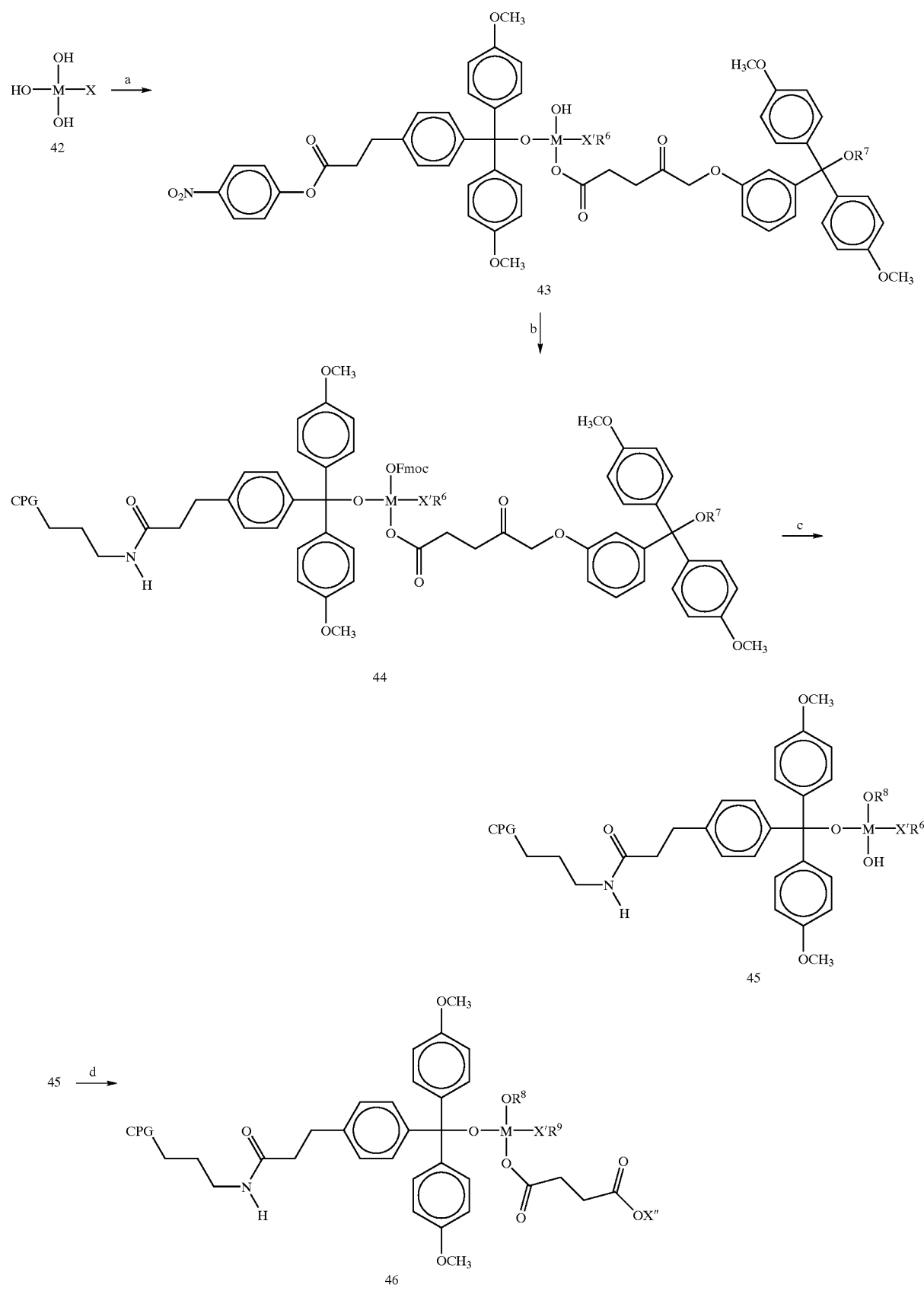

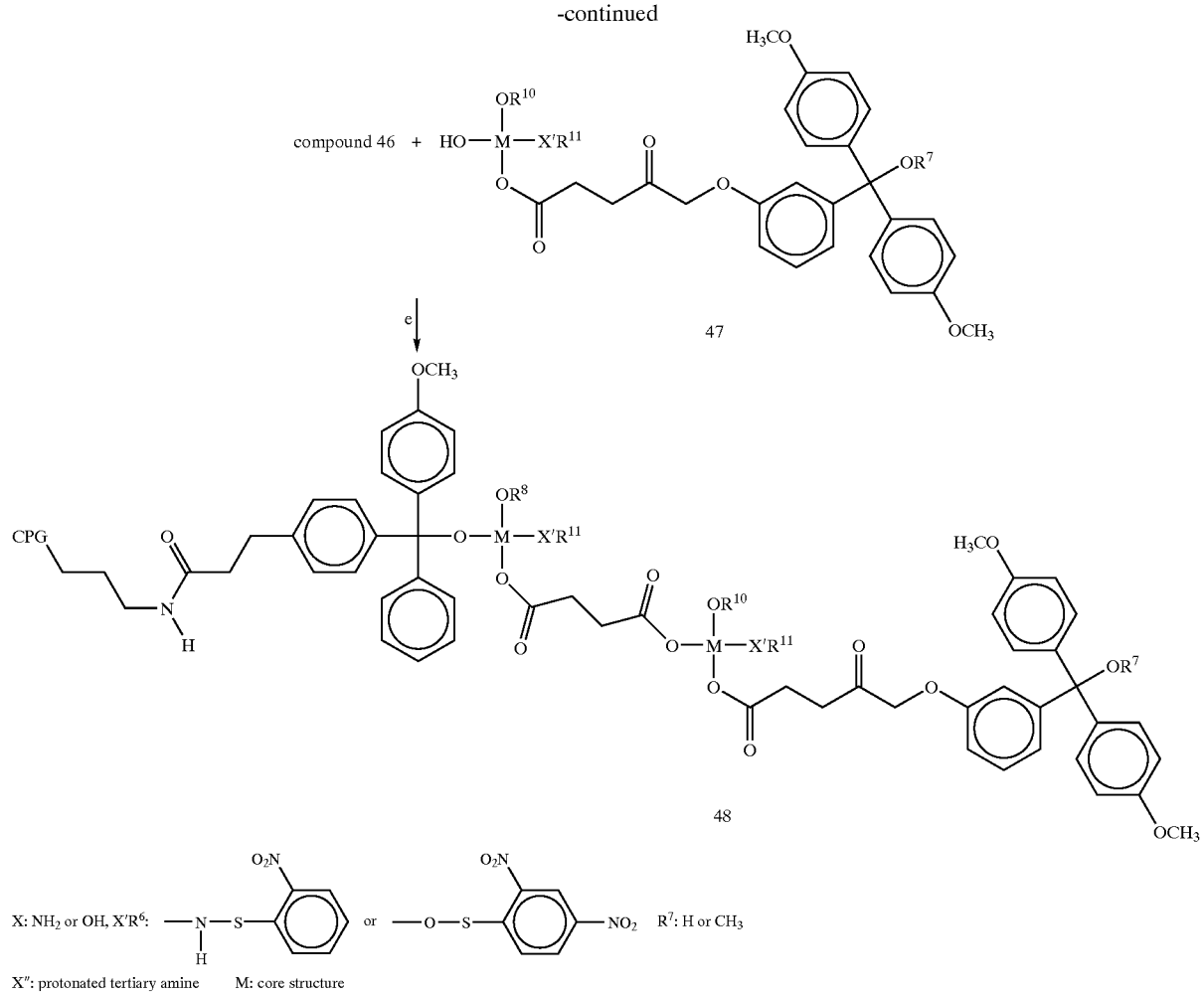

Description of Scheme 9:

a: protection of compound 42 with 39 (scheme 8), 32 (scheme 7)1),),4-dinitro- or 2-nitrophenylsulfenyl chloride b: aminolysis with aminopropyl CPG, followed by reaction with Fmoc chloride c: orthogonal deprotections of the Fmoc (9-fluorenylmethoxycarbonyl) group and group $R^6$ and derivatizations with new substituents $R^8$ and $R^9$ respectively, orthogonal deprotection of the levulinic ester moiety d: reaction with succinic anhydride e: reaction of compound 46 with 47. Compound 47 is (as compound 46) a derivative of compound 44 but otherwise derivatized (with new substituents $R^{10}$ and $R^{11}$ in compound 47 in contrast to $R^8$ and $R^9$ in 46). 47 was removed from the support. The reaction to 48 can be carried out as described by Gupta, K. C. et a)., *Nucl. Acids Res.*, 1991, 19, 3019–25. The successful reaction to 48 can be monitored by vis spectroscopy of 48 after treatment with acid.

1) After substitution with compound 32 the tertiary OH functionality can be methylated.

Scheme 9 shows a general way to easily create a high number of derivatives. Compound 43 could be obtained e.g. by successive monosubstitutions using a substantial excess of compound 42 and its products respectively with 39 (scheme 8), 32 (scheme 7), 2,4-dinitrophenysulfenyl (dnps) chloride or 2-nitrophenyl sulfenyl (nps) chloride (order not obligatory). An excess of 42 can apparently be avoided if regioselective reagents such as 39 are employed. If 42 has an amino function (X=NH$_2$), transient protection of the OH groups e.g. with trimethylsilyl chloride followed by protection of the amino function with nps chloride are the first steps. A great excess of 42 should not be necessary in this case.

The structure of the protecting groups is very useful for the reaction control by thin layer chromatography (tlc) during the synthesis of compound 43. Each reaction step can be controlled by a specific colorimetric effect and UV-detection. This is demonstrated by the following description. If a compound 42 with e.g. four hydroxyl groups is monosubstituted by compound 32 (scheme 7), treatment with acid leads to an orange product (trityl cation), but the colorimetric trityl moiety is not cleaved. After the second monosubstitution with 39 (scheme 8), detection with acid leads to two orange products, because one of the trityl moieties is now cleaved off. Additionally, intensive yellow color can be observed by ammonia vapour (or by primary and secondary amines), due to released p-nitrophenolate ions. The product obtained after the third monosubstitution with dnps chloride already shows yellow color without any detection reagent (and of course the other colorimetric effects). Protection of the last free hydroxyl group with Fmoc chloride should be done after the reaction of compound 43 with aminopropyl CPG, because of the sensitivity of Fmoc esters in the presence of amino groups. Nevertheless, the last free hydroxyl group of a sample of compound 43 can be substituted by a nucleoside derivative (the reactive form of 5'-O-DMTr-T$_d$-O3'-succinic mono ester e.g.). By contact with sugar spray reagent and heating with a fan an additional green colored product can be observed on tlc (due to the superposition of the blue color of the nucleoside and the orange color of the trityl moieties). This shows the possibility to control four successive monosubstitions by different colorimetric effects.

Generalized, the introduction of 39 (scheme 8), 32 (scheme 7) and 2,4-dinitrophenylsulfenyl (dnps) chloride or 2-nitrophenylsulfenyl (nps) chloride and the selective/orthogonal deprotections of the corresponding protecting groups in a chosen multifunctional molecule can be controlled by different colorimetric effects in each step.

Scheme 10

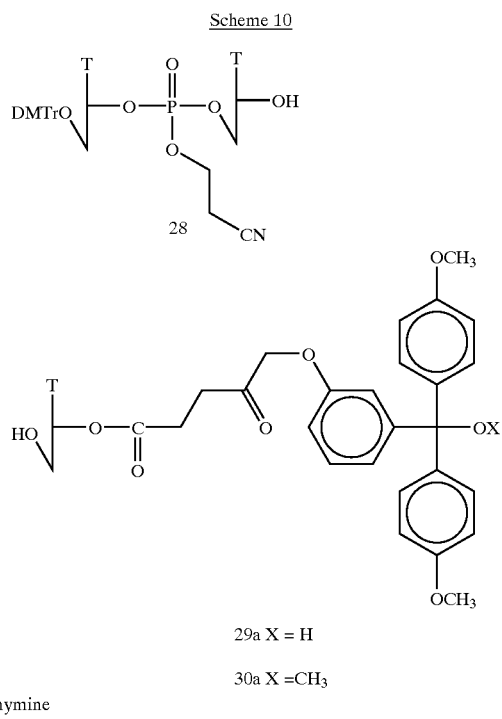

29a X = H

30a X = CH$_3$

T : thymine

The present invention is further illustrated by the following examples which should not be construed as limiting in any way. The contents of all cited references (including literature references, issued patents, published patent applications and co-pending patent applications, as cited throughout this application are hereby expressly incorporated by reference.

EXAMPLES

Materials and Methods $^1$H (400 and 250 MHz) and $^{13}$C )101 and 63 MHz) NMR spectra were recorded on a Bruker AMX 400 and a AC 250-P instrument. Samples were dissolved in the presence of tetramethylsilane as internal standard, unless otherwise stated. $^{31}$P NMR spectra were recodered on a Varian Gemini 200 instrument. Internal standard: phosphoric acid in the solvent used for the sample (δ=0.00 ppm), Chemical shifts are given in ppm. Mass spectra were obtained on a Finnigan MAT 311A mass spectrometer under EI conditions, a VG Analytical 70–250S mass spectrometer under FAB conditions (matrix: 3-nitro-benzyl alcohol, Xenon bombardment) and a Finnigan MAT Vision 2000 mass spectrometer under MALDI-TOF conditions (matrix solution: 0.7 mol/l 3-hydroxy picolinic acid and 0.07 mol/l ammonium citrate in acetonitrile/water, 1/1, v/v). Elementary analyses were performed by the analytical department of the Institute of Organic Chemistry, University of Hamburg. Thin layer chromatography (tlc) was carried out on 60 PF$_{254}$ silica gel coated alumina sheets (Merck, Darmstadt, No 5562). Trityl and sugar containing compounds are visualized with sugar spray reagent (0.5 ml 4-methoxybenzaldehyde, 9 ml ethanol, 0.5 ml concentrated sulfuric acid and 0.1 ml glacial acetic acid) by heating with a fan or on a hot plate. p-Nitrophenyl ester containing compounds are visualized by ammonia vapour. Column chromatography was performed using silica gel from Merck. HPLC results were obtained on a Waters chromatography systems 625 LC with a photodiodearray detector 996 and using reversed phase columns (Waters Nova-Pak C18, 60 Å, 4 μm particles, 3.9×300 mm, software: Millenium 2.0, eluants were: 0.1 M triethylammonium acetate at pH 7.0 (A) and acetonitrile (B); the column was equilibrated at 30° C. at 1 ml per min, with 95% A/5% B, v/v, with elution using a linear gradient from 5% to 40% B in 40 min, monitored at 254 nm). Spectrophotometric measurement in the UV/Vis region were performed on a Beckman UV35 and a LKB Ultrospec Plus UV/Vis spectrophotometer. Solvents were dried and purified before use according to standard procedures. Extractions were monitored by tlc to optimize completion of extraction.

Example 1

3'-O-levulinyl Esters of the Nucleosides 30a–d (Building Block 2)

Compound 32 was prepared in situ by reacting levulinic acid derivate 31 (Leikauf, E., Köster. H., Tetrahedron, 1995, 51, 5557–62) (3.78 g, 8.39 mmol) with N,N'dicyclohexylcarbodiimide (1.80 g, 8.74 mmol) in dry dioxane (25 ml). N,N'-dicyclohexylurea is removed by filtration and washed with dioxane. The solution was divided in four equal parts and the solvents were evaporated in vacuo. To each of the four residues of anhydride 32 was added one of the four following protected nucleosides: 5-O-DMTr-2'-deoxythymidine, 5'-O-DMTr-N$^4$-npeoc-2'-deoxycytidine, 5'-O-DMTr-N$^6$-npeoc-2'-deoxyadenosine, 5'-O-DMTr-N$^2$-npeoc-O$^6$npe-2'-deoxyguanosine (1.00 mmol of each; base protected deoxynucleosides were from Chemogen, Konstanz) (Stengele, K. P., Pfleiderer, W., Tetrahedron Lett., 1990, 31, 2549–52) and 4-dimethylaminopyridine (0.0100 g, 0.0819 mmol) in 1.64 ml pyridine. Completion of reaction was checked by thin layer chromatography. 30 min after the addition of a mixture of 0.130 ml of glacial acetic acid and 0.245 ml pyridine, 0.046 ml water were added, 60 min later an excess of ethyl acetate was added, the N,N'-dicyclohexyluree removed by filtration and washed with ethyl acetate. The mixture was extracted with water, 5% aqueous sodium hydrogen carbonate and water. After drying with sodium sulfate, the solvent was evaporated, then co-evaporated with toluene. The residues were directly detritylated with 80% acetic acid and the reaction was monitored by thin layer chromatography. The solutions were poured into an excess of water (about 10 fold) and the aqueous mixtures were extracted with ethyl acetate. The organic phase was washed with 5% aqueous sodium hydrogen carbonate and water. After drying the solvent was evaporated, then co-evaporated with toluene (to remove remaining acetic acid). The residues were directly methylated by adding to each a solution of 200 ml methanol and 1 ml glacial acetic acid. If there were some insoluble material, it was dissolved in 5–10 ml dichloromethane and a mixture of 100 ml methanol and 0.5 ml glacial acetic acid was added. Monitoring by thin layer chromatography indicates completion of the reaction. The solvents were evaporated under reduced pressure, followed by co-evaporation with toluene (2–3 times). The residues of 30a–d were purified by silica gel column chromatography (30a: silica gel 60H, No. 7736, 30b–d: silica gel 60, No. 9385; Merck, Darmstadt). Silica gel used per gram raw product: 30a: 25 g, 30b: 51 g, 30c: 65 g, 30d: 51 g; using a step gradient from dichloromethane to dichloromethane/methanol 98/2 (v/v), in the presence of 0.1% pyridine. Pure fractions were pooled, the solvents removed by evaporation, the residues dissolved in dichloromethane (15 ml per gram residue) and the solutions precipitated into hexane (315 ml per gram residue). Yields: 30a: 68%, 30b: 63%, 30c: 62%, 30d: 52%.

Compound 30a: $^1$HNMR (400 MHz, CDCl$_3$): δ=1.88 (s, 3H, —C$\underline{H}_3$ of thymine), 2.5–2.34 (m, 2H, H2$^{1a}$/H2$^{ib}$), 2.64 (t, 2$\underline{H}$, —CH$_2$—CH$_2$—), 2.93 (t, 2$\underline{H}$, —C$\underline{H}_2$—CH$_2$—), 3.04)s, 3H, R$_3$ C—OC$\underline{H}_3$), 3.8 (s, 6H, aryl-OC$\underline{H}_3$), 3.9 (m, 2H, H5$^{1a}$/H5$^{ib}$), 4.1 (m 1H, H4'), 4.57 (s, 2H, —CO—C$\underline{H}_2$—O—), 5.38 (m, 1H, H3'), 6.26 (t, 1H, H1'), 7.34–6.7 (m, 12H, aryl-$\underline{H}$), 7.55 (s, 1H, H6), 8.93 (s, 1H, N—$\underline{H}$ of thymine). -$^{13}$C NMR (101 MHz, CDCl$_3$): δ=12.51 (q, —C$\underline{H}_3$ of thymine), 27.43 (t, —C$\underline{H}_2$—CH$_2$—), 33.79 (t, —CH$_2$—C$\underline{H}_2$—), 37.27 (t, C2'), 51.92 (q, R$_3$C—OC$\underline{H}_3$), 55.23 (q, aryl-OC$\underline{H}_3$), 62.39 (t, C5'), 72.77 (t, —CO—C$\underline{H}_2$—O—), 75.31 (d, C3'), 85.20 (d, C4'), 85.92 (d, C1'), 86.31 (s, R$_3\underline{C}$—OCH$_3$), 111.28 (s, C5 of thymine), 112.37, 113.11, 114.59, 121.83, 128.95, 130.20 (d, $\underline{C}$—H, aryl), 135.63, 147.58 (s, R$_2\underline{C}$—CR$_2$—OCH$_3$, aryl, quaternary), 136.34 (d, C6 of thymine), 150.52 (s, C2 of thymine), 157.32, 158.52 (s, R$_2\underline{C}$—OCH$_3$, and s, R$_2\underline{C}$—O—CH$_2$CO—, aryl, position not defined), 163.69 (s, C4 of thymine), 172.26 (s, —$\underline{C}$OOR), 206.02 (s, $\underline{C}$O —). -$^1$H$^1$H and $^1$H$^{13}$C 2D NMR spectra were determined. -MS (FAB, pos mode): m/z (rel. intensity): m/z calculated for C$_{37}$H$_{40}$N$_2$O$_{11}$ (M$^+$): 688; found: 688 (7), 657 (74, M —OCH$_3^+$), 391 (78), 307 (100). -Elementary Analysis (%): Found: C, 64.99/64.73; H, 5.98/5.82; N, 4.02/3.99; C$_{37}$H$_{40}$N$_2$O$_{11}$ requires C, 64.53; H, 5.85; N, 4.07.

Compound 30b: $^1$HNMR (400 MHz, CDCl$_3$); δ=2.38 (m, 1H, H2$^{1a}$), 2.65 (m, 1H, H2$^{1b}$, t, 2H, —CH$_2$—C$\underline{H}_2$—, 3'-OH protecting group), 2.9 (t, 2H, —CH$_2$—CH$_2$—, 3'OH protecting group), 3.04 (s, 3H, R$_3$C—OC$\underline{H}_3$), 3.1 (t, 2H, —C$\underline{H}_2$—CH$_2$—, base protection), 3.8 (s, 6H, aryl-OCH$_3$), 3.99–3.88 (m, 2H, H5$^{1a}$/H5$^{1b}$), 4.19 (m, 1H, H4'), 4.44 (t, 2H, —CH$_2$—C$\underline{H}_2$—base protection), 4.55 (s, 2H, —CO—CH$_2$—O—), 5.38 (m, 1H, H3'), 6.26 (m, 1H, H1'), 7.34–6.7 (m, 13H, aryl-$\underline{H}$ and H5), 7.38 (d, 2H, O$_2$N-aryl-$\underline{H}$, meta), 8.17 (d, 2H, O$_2$N-aryl-$\underline{H}$, ortho), 8.3–8.2 (s, 1H, N—$\underline{H}$ and d, 1H, H6 of cytosine). -$^{13}$CNMR (101 MHz, CDCl$_3$): δ=27.43 (t, —C$\underline{H}_2$—CH$_2$—, 3'-OH protecting group), 33.78 (t, —C$\underline{H}_2$—CH$_2$—, 3'-OH protecting group), 34.97 (t, —C$\underline{H}_2$—CH$_2$—, base protection), 38.58 (t, C$_2$'), 51.91 (q, R$_3$C—OC$\underline{H}_3$), 55.23 (q, aryl-OC$\underline{H}_3$), 62.12 (t, C$_5$'), 65.49 (t, —CH$_2$—C$\underline{H}_2$)—, base protection). 72.76 (t, —CO—C$\underline{H}_2$—O—), 74.98 (d, C3'), 85.98 (d, C4' and d, C1'), 123.86 (d, $\underline{C}$—H, O$_2$N-aryl, ortho), 129.77 (d, $\underline{C}$—H, O$_2$N-aryl, meta), 112.35, 113.1, 114.58, 121.83, 128.95, 130.2 (d, $\underline{C}$—H, aryl, d, C5 and d, C6 of cytosine, position not defined), 86.31 (s, R$_3\underline{C}$—OCH$_3$), 123.22, 135.64, 147.58, 149.14, 149.40, 149.67 (s, aryl, quaternary, C2, C4 of cytosine and —NH—$\underline{C}$O— of the base protection, position not defined), 157.32, 158.52 (s, R$_2\underline{C}$OCH$_3$, and s, R$_2\underline{C}$—O—CH$_2$—CO—, aryl, position not defined), 172.32 (s, —$\underline{C}$OOR), 205.97 (s, —$\underline{C}$O—). -$^1$H$^1$H and $^1$H$^{13}$C 2D NMR spectra were determined. -MS (FAB, pos. mode): m/z (rel. intensity): m/z calculated for C$_{45}$H$_{46}$N$_4$O$_{14}$ (M$^+$): 866; found: 866 (9), 835 (100, M —OCH$_3^+$), 307 (87).

Compound 30c: $^1$HNMR (400 MHz, CDCl$_3$): δ=2.48 (m, 1H, H2$^{1a}$), 2.67 (t, 2H, —C$\underline{H}_2$—CH$_2$—, 3'-OH protecting group), 2.96 (t, 2H, —CH$_2$—C$\underline{H}_2$—, 3'-OH protecting group 3.05 (s, 3H, R$_3$C—OC$\underline{H}_3$), 3.15 (t, 2H, —C$\underline{H}_2$—CH$_2$—, base protection and m, 1H, H2$^{ib}$) 3.78 (s, 6H, aryl-OC$\underline{H}_3$), 4.0–3.84 (m, 2H, H5$^{1a}$/H5$^{1b}$), 4.29 (m, 1H, H4'), 4.55 (t, 2H, —CH$_2$—C$\underline{H}_2$—, base protection and s, 2H, —CO—C$\underline{H}_2$—O—), 5.58 (m, 1H, H3'), 6.35 (m, 1H, H1'), 7.34–6.7 (m, 12H, aryl$\underline{H}$ of DMTr), 7.42 (d, 2H, O$_2$N-aryl$\underline{H}$, meta), 8.08 (s, 1H, H2 or H8 of adenine), 8.14 (d, 2H, O$_2$N-aryl-$\underline{H}$, ortho), 8.73 (s, 1H, H2 or H8 of adenine), 9.04 (—N—$\underline{H}$ of adenine), -$^{13}$CNMR (101 MHz, CDCl$_3$): δ=27.49 (t, —C$\underline{H}_2$—CH$_2$—, 3'-OH protecting group), 33.86 (t, —C$\underline{H}_2$—CH$_2$—, 3'-OH protecting group), 35.01 (t, —C$\underline{H}_2$—CH$_2$—, base protection), 37.85 (t, C2'), 51.91 (q, R$_3$C—OC$\underline{H}_3$), 55.22 (q, aryl-OC$\underline{H}_3$), 63.16 (t, C5'), 65.52 (t, —CH$_2$—C$\underline{H}_2$—, base protection), 72.77 (t, —CO—C$\underline{H}_2$—O—), 76.57 (d, C3'), 87.25 (d, C4'), 87.49 (4, C1'), 123.84 (d, $\underline{C}$—H, O$_2$N-aryl, ortho), 112.32, 113.11, 114.55, 121.87, 135.57, 145.24, 147.02, 147.72, 149.18, 149.72, 150.04, 150.69 (s, aryl, quaternary, C4–6 of adenine and —NH—$\underline{C}$O— of the base protection, position not defined), 142.31 (d, C2 or C8 of adenine), 152.3 (d, C2 or C8 of adenine), 157.3, 158.54 (s, R$_2$—$\underline{C}$—OCH3, and s, R$_2\underline{C}$—O—CH$_2$—CO—, aryl, position not defined), 171.98 (s, —COOR), 206.14 (s, —$\underline{C}$O—). -$^1$H $^1$H and $^1$H$^{13}$C 2D NMR spectra were determined. -MS (FAB, pos. mode): m/z (rel. intensity): m/z calculated for C$_{46}$H$_{46}$N$_6$O$_{13}$ (M$^+$): 890; found: 859 (5, M —OCH$_3^+$), 307 (100). -Elementary Analysis (%): Found: C, 62.14/62.00; H, 5.26/5.17; N, 9.06/9.01; C$_{46}$H$_{46}$N$_6$O$_{13}$ requires C, 62.02; H, 5.20; N, 9.43.

Compound 30d: $^1$HNMR (400 MHz, CDCl$_3$): δ=2.44–2.40 (m, 1H, H2$^{'a}$), 2.67 (t, 2H —C$\underline{H}_2$—CH$_2$—, 3'-OH protecting group), 2.96 (t, 2H, —CH$_2$—C$\underline{H}_2$—, 3'-OH protecting group), 3.04 (s, 3H, R$_3$C—OC$\underline{H}_3$), 3.12 (t, 2H, —C$\underline{H}_2$—CH$_2$—, npeoc base protection and m, 1H, H2$^{ib}$, 3.30 (t, 2H, —C$\underline{H}_2$—CH$_2$—, npe base protection), 3.8 (s, 6H, aryl-OC$\underline{H}_3$), 3.99–3.82 (m, 2H, H5$^{'a}$/H5$^{'b}$), 4.23 (m, 1H, H4'), 4.49 (t, 2H, —CH$_2$—C$\underline{H}_2$—, npeoc base protection)) 4.56 (s, 2H, —CO—C$\underline{H}_2$—O—), 4.82 (t, 2H, —C$\underline{H}_2$—CH$_2$—, npe base protection 5.57 (m, 1H, H3'), 6.24 (m, 1H, H1), 7.7–6.7 (m, 16H, aryl-$\underline{H}$ of DMTr, O$_2$N-aryl-$\underline{H}$, meta and s, 1H, —N—$\underline{H}$ of guanine), 7.89 (s, 1H, H8 of guanine). 8.18–8.13 (m, O$_2$N-aryl-$\underline{H}$, ortho, npe and npeoc group). -$^{13}$C NMR (101 MHz, CDCl$_3$): δ=27.46 (t, —C$\underline{H}_2$—CH$_2$—, 3'-OH protecting group)) 33.86 (t, —CH$_2$—C$\underline{H}_2$—, 3'-OH protecting group), 35.04 (t, —C$\underline{H}_2$—CH$_2$, npe and npeoc base protection), 37.37 (t, C2'), 51.92 (q, R$_3$C—OC$\underline{H}_3$) 55.23 (q, aryl-OC$\underline{H}_3$), 63.01 (t, C5'), 64.97 (t, —CH$_2$—C$\underline{H}_2$—, npeoc base protection), 67.07 (t, —CH$_2$—C$\underline{H}_2$—npe base protection), 72.77 (t, —CO—C$\underline{H}_2$—O), 76.24 (d, C3'), 86.55 (d, C4'), 86.79, (d, C1'), 123,75, 123.82 (d, $\underline{C}$—H, O$_2$N-aryl, ortho, npe and npeoc base protection, position not defined), 141.33 (d, C8 of guanine), 112.32, 113.11, 114.55, 121.87, 128.96, 129.77, 130.04, 130.21 (d, $\underline{C}$—H, aryl), 86.30 (s, R$_3\underline{C}$—OCH$_3$,), 135.58, 145.58, 146.94, 147.7, 149.15, 149.42, 149.69, 151.13, 151.47, 152.06, 161.01 (s, aryl, quaternary, C2, C4–6 of guanine and —NH—$\underline{C}$O of the base protection, position not defined), 157.31, 158.54 (s, R$_2\underline{C}$—OCH$_3$, and s, R$_2\underline{C}$—O—CH$_2$—CO—, aryl, position not defined), 172.04 (s, —$\underline{C}$OOR), 206.10 (s, —$\underline{C}$O—). -$^1$H$^1$H and $^1$H$^{13}$C 2D NMR spectra are determined. -MS (FAB, pos. mode): m/z (rel. intensity): m/z calculated for C$_{54}$H$_{53}$N$_7$O$_{16}$ (M$^+$): 1055; found: 1024 (6, M —OCH$_3^+$), 307 (100).

Example 2
Phosphoamidites 2a–d (Building Block 2)

All steps were carried out under inert atmosphere (argon). Organic solvents were free from water and other impurities. Compounds 30a–d (0.5 mmol of each) were azeotropically dried with small amounts of pyridine and toluane and dissolved in 2.43 ml ethyl acetate. After the addition of N,N-diisopropyl ethylamine (1 .75 mmol, 0.226 g, corresponding to 0.30 ml at room temperature) the reaction flask was capped with a septum and cooled with an ice bath. Chloro-β-cyanoethoxy-N,N-diisopropylaminophosphane (0.610 mmol, 0.144 g, corresponding to 0.117 ml at room temperature, Biosyntech, Hamburg) was added dropwise by a syringe. 15 min later the reaction was allowed to raise to room temperature. Monitoring by thin layer chromatography (about 60 min after starting the reaction) indicated complete conversions to the amidites 2a–d. The precipitated amine hydrochloride was filtered off using a column type reactor fitted with a sintered glass fritt and washed with 1 .5 ml ethyl acetate. The solution was extracted in a separation funnel with cold 5% sodium hydrogen carbonate (2×2.8 ml). The organic solution was filtered using the described reactor which contains sodium sulfate, followed by washing of the sodium sulfate layer with ethyl acetate (2×1.8 ml). After evaporation of the solvents of the filtrate, a foam was obtained. The amidite was dissolved in 5 ml ethyl acetate (containing 0.1% pyridine) and precipitated into 120 ml of hexane (at −20° C.). After filtration using the described reactor the amidite was washed with 12 ml of hexane, dried and stored at 20° C. Yields: 2a: 86%, 2b: 72%, 2c: 78%, 2d: 80%. -$^{31}$ P NMR (81 MHz, CD$_3$CN/CH$_3$CN, I/I,v/v and a trace of N,N-diisopropyl ethylamine): 2a: δ=149.18, 149.35 (diastereomers), 2b: δ=149.25, 2c: δ=149.07, 2d: δ=148.89, 149.16 (diastereomers).

Example 3
3-(4-Formylphenyl)-propionic acid (35) (Building Block 1)

Hydrogenation of compound 34 (Pohl, H., *J. prakt. Chem.*, 1934, 141, 45–60; Skita, A., Ritter, H., *Ber. Dtsch, Chem. Ges.*, 1910, 43, 3393–99; Paal, C., Harmann, W., *Ber. Dtsch. Chem. Ges.*, 1909, 42, 3930–39) was carried out in the presence of 5% Pd on activated carbon. -$^1$H NMR (250 MHz, [D$_6$]DMSO): δ=2.6 (t, 2H, —CH$_2$—CH$_2$—), 2.95 (t, 2H, CH$_2$—CH$_2$,), 7.45 (d, 2H, H-aryl-CHO, meta), 7.85 (d, 2H, H-aryl-CHO, ortho, 9.96 (s, 1H, —CHO), 12.16 (s, 1H, —COOH).

Example 4
3-{4-[Bis-(4-methoxyphenyl)-methyl]-phenyl}-propionic acid (36) (Building Block 1)

Compound 35 (25.7 g, 144 mmol) and methoxybenzene (36.8 g, 340 mmol) were stirred in 450 ml glacial acetic acid to dissolve most of the material. The mixture was cooled in an ice bath and immediately concentrated sulfuric acid (225 g, 2290 mmol) added dropwise. The reaction mixture was then stirred at room temperature until thin layer chromatography (dichloromethane/methanol: 8/2, v/v) demonstrated quantitative conversion. The reaction mixture was poured into 3/1 ice/water. Subsequently the reaction flask was washed with ether and the ether solution was poured into the ice/water. The orange-white raw product between the aqueous and organic layer was filtrated by suction (if there was still a considerable amount of the raw product under the aqueous and/or dissolved in the ether layer, it was also worked up). The raw product was triturated with 200 ml water, filtrated by suction, again triturated with petroleum ether (bp 60–70° C.) and filtrated. It was recrystallized from ether. Yield: 22.3 g (41%). Note: More product 36 can be purified from the crystalline residue of the mother liquor by silica gel column chromatography or by Soxhlet extraction with petroleum ether (bp 30–50° C). $^1$H NMR (250 MHz, CDCl$_3$): δ=2.65 (t, 2H, —CH$_2$—CH$_2$—), 2.92 (t, 2H, —CH$_2$—CH$_2$—l),3.78 (s, 6H, —OCH$_3$), 5.40 (s, 1H, R$_3$C—H), 7.13–6.77 (m, 12H, aryl-H), -$^{13}$C NMR (63 MHz, CDCl$_3$, internal standard CDCl$_3$, at 77.00 ppm): δ=30.1 (t, —CH$_2$—CH$_2$—), 35.48 (t, —CH$_2$—CH$_2$—), 54.8, 55.19 (q, aryl—OCH$_3$ and d, R$_3$, C—H, position not defined), 113.63, 128.1, 129.41, 130.21 (d, CH, aryl), 136.46, 137.91, 142.7 (s, aryl, quartenary), 157.93 (s, R$_2$C—OCH$_3$, aryl), 178.85 (s, —COOH).—MS (El): m/z (rel. intensity): m/z calculated for C$_{24}$H$_{24}$O$_4$ (M$^+$): 376; found: 376 (100), 345 (9, M—OCH$_3$$^+$), 227 (35, M—HOOC—CH$_2$—CH$_2$—C$_6$H$_4$$^+$). —MS (FAB, pos. mode): m/z (rel. intensity): m/z calculated for C$_{24}$H$_{24}$O$_4$ (M$^+$): 376; found: 376 (48), 345 (8, M—OCH$_3$$^+$), 269 (53, M—C$_6$H$_4$—OCH$_3$$^+$), 227 (38, M—HOOC—CH$_2$—CH$_2$—C$_6$H$_4$$^+$), -Elementary Analysis (%): Found: C, 76.55/76.35; H, 6.71/6.53; C$_{24}$H$_{24}$O$_4$ requires C, 76.57; H, 6.43.

Example 5
p-Nitrophenyl-3-{4-[bis-(4-methoxyphenyl)-methyl]-phenyl}-propionate (37) (Building Block 1)

Compound 36 (22.2 g, 59.0 mmol) and p-nitrophenol (8.23 g, 59.2 mmol) were dissolved in dry dioxane (272 ml) and dry pyridine (14.7 ml). After addition of a solution of N,N'-dicyclohexylcarbodiimide (13.9 g, 67.4 mmol) in dry dioxane (66 ml) the mixture was stirred at room temperature until thin layer chromatography (dichloromethane/methanol: 9/1, v/v) revealed quantitative conversion (4–18 h). N,N'-Dicyclohexylurea was removed by filtration, the precipitate washed with dioxane until no UV absorbing material could be detected. The solvent was evaporated, the residue azeotropically dried with toluene, dissolved in dichloromethane (70 ml) and remaining dicyclohexylurea removed by filtration. After evaporating the solvent, the residue was directly converted to compound 38. Remaining DCC could be removed with a small amount of hexane. Yield: 29.1 g (99%). -$^1$H NMR (250 MHz, CDCl$_3$):δ=2.90 (t, 2H, —CH$_2$—CH$_2$—), 3.14 (t, 2H, —CH$_2$—CH$_2$—), 3.78 (s, 6H, —OCH$_3$), 5.43 (s, 1H, R$_3$C—H), 7.18–6.76 (m, 14H, aryl-H), 8.22 (d, 2H, O$_2$N-aryl-H, ortho). -$^{13}$C NMR (63 MHz, CDCl$_3$): δ=30.42 (t, —CH$_2$—CH$_2$—), 35.9 (t, —CH$_2$—CH$_2$—), 54.88 (d, R$_3$C—H), 55.24 (q, aryl-OCH$_3$), 113.69, 122.43, 125.17, 128.31, 129.57, 130.24 (d, C—H, aryl), 136.39, 137.38, 143.14, 145.32, 155.35 (s, aryl, quartenary), 158.02 (s, R$_2$C—OCH$_3$, aryl), 170.5 (s, —COOR). -MS (EI): m/z (rel. intensity): m/z calculated for C$_{30}$H$_{27}$NO$_6$ (M$^+$): 497; found: 497 (16), 480 (3), 51(100). -MS (FAB, pos. mode): m/z (rel. intensity): m/z calculated for C$_{30}$H$_{27}$NO$_6$ (M$^+$): 497; found: 497 (26), 466 (4, M—OCH$_3$$^+$), 390 (45, M—C$_6$H$_4$—OCH$_3$$^+$), 375 (24, M—O$_2$N—C$_6$H$_4$$^{30}$), 227 (100, M—O$_2$N—C$_6$H$_4$—OOC—CH$_2$—CH$_2$—C$_6$H$_4$$^+$).

Example 6
p-Nitrophenyl-3-{4-[bis-(4-methoxyphenyl)-hydroxymethyl]-phenyl}-propionate (38) (Building Block 1)

Compound 37 (29.1 g, 58.5 mmol) was dissolved in 670 ml glacial acetic acid and freshly prepared lead dioxide (Rotermund, G. W., *Methoden der organischen Chemie* (*Houben-Weyl*), vol. IV/1b, Oxidation, part 2; Georg Thieme Verlag, Stuttgart 1975, pp.176) (9.95 g, 41.6 mmol) was added and the mixture placed in a preheated oil bath until a clear solution was obtained. Another 9.95 g (41.6 mmol) lead dioxide was added and dissolved. The reaction was monitored by thin layer chromatography (dichloromethane/methanol 99/1, v/v). During the reaction a side product appeared which traveled between the educt 37 and product 38. The reaction was terminated when UV intensity of the residual 37 spot equaled the side product. The reaction mixture was poured on ice/water (31) and extracted with dichloromethane. The organic layer was extracted with water and dried with $Na_2SO_4$. Solvents were evaporated and some remaining acetic acid removed by co-evaporation with toluene. The raw product (29.8 g) was dissolved in dichloromethane and purified by silica gel 60H (Merck, Darmstadt; No.7736, 1200 g) column chromatography; elution was carried out in the presence of 0.03% pyridine using a step gradient from dichloromethane to dichloromethane/ethanol 99/1, v/v). Fractions containing compound 38 were combined and the solvents evaporated. The sirupous residue gradually crystallized under a petroleum ether layer after rubbing with a glass rod Yield: 15.1 g (50%). 2.15 g (7%) of the starting material 37 was recovered. -$^1$H NMR (250 MHz, $CDCl_3$). δ=2.70 (s, 1H, $R_3C$—O$\underline{H}$), 2.94 (t, 2H, —C$\underline{H}_2$—$_{CH_2}$—)3.1 (t, 2H, —CH$_2$—C$\underline{H}_2$—), 3.78 (s, 6H, —OC$\underline{H}_3$), 7.28–6.78 (m, 14H, aryl-$\underline{H}$), 8.21 (d, 2H, $O_2N$-aryl-$\underline{H}$, ortho). -$^{13}$C NMR (63 MHz, $CDCl_3$): δ=30.37 (t, —C$\underline{H}_2$—CH$_2$—), 35.8 (t,—CH$_2$—C$\underline{H}_2$—), 55.26 (q, aryl-OC$\underline{H}_3$), 81.27 (s, $R_3\underline{C}$—OH), 113.22, 122.41, 125.17, 127.87, 128.08, 129.08, (d, $\underline{C}$—H, aryl), 138.35, 139.41, 145.32, 145.85, 155.32 (s, aryl, quarternary), 158.7 (s, $R_2\underline{C}$—OCH$_3$, aryl), 170.45 (s, —$\underline{C}$OOR). -MS (EI): m/z (rel. intensity): m/z calculated for $C_{30}H_{27}NO_7$ (M$^+$): 513 found: 513 (22), 496 (9, M—OH$^+$), 406 (12, M—$C_6H_4$—OCH$_3^+$), 243 (93, M—$O_2N$—$C_6H_4$—OOC—CH$_2$—CH$_{2\text{-}C_6}H_4^+$), 135 (100). -MS (FAB, pos. mode): m/z (rel. intensity): m/z calculated for $C_{30}H_{27}NO_7$ (M$^+$):513; found: 513 (19), 496 (90, M—OH$^+$),406 (16, M—$O_2N$—$C_6H_4$—OCH$_3^+$), 391 (11, M—$O_2N$—$C_6H_4^{+}$, 375 (3, M—$O_2N$—$C_6H_4$—O—$^+$), 243 (52, M—$O_2N$—$C_6H_4$—OOC—CH$_2$—CH$_{2\text{-}C_6}H_4^{+}$, 135 (100). -Elementary Analysis (%): Found: C, 70.47/70.78; H, 5.35/5.38; N, 2.75/2.74; $C_{30}H_{27}NO_7$ requires C, 70.16; H, 5.3; N, 2.73.

Example 7
p-Nitrophenyl-3-{4-[bis-(4-methoxyphenyl)-chlormethyl]-phenyl}propionate (39) (Building Block 1)

Compound 38 (0.600 g, 1.17 mmol) was refluxed in acetyl chloride (6 ml) for 3 h. Solvents were evaporated and remaining traces of acetic acid or/and acetyl chloride removed by co-evaporation with toluene. The residue was directly converted to compound 40.

Example 8
Alcoholysis of Compound 39 with 30a to Compound 40 (Building Block 1)

The sirupous raw product of compound 39 (max. 1.17 mmol) was dissolved in dry pyridine (4.1 ml) and compound 30a (0.450 g, 0.653 mmol) was added. After 19 h another 0.140 g (0.203 mmol) 30a was added. 24 h later monitoring by thin layer chromatography indicated no further conversion. Pyridine (3 ml) and ethanol (0.3 ml) were added and the solution poured into an excess of water after 5 min. The water solution was extracted with ethyl acetate. The organic phase was extracted with water and dried with $Na_2SO_4$— Solvents were evaporated and the residue azeotropically dried with toluene. The raw product (1.38 g) was dissolved in dichloromethane and purified by silica gel 60 (Merck, Darmstadt; No.9385, 80 g) column chromatography; elution was carried out in presence of 0.1% pyridine with dichloromethane/ethanol 99/1, v/v). Fractions containing 40 were combined and the solvents evaporated. The residue was dissolved in dichloromethane (11 ml) and precipitated into hexane (220 ml). Yield: 0.468 g (46%). -$^1$H NMR (400 MHz, $CDCl_3$ and a trace of [$D_5$]pyridine): δ=1.36 (s, 3H, —C$\underline{H}_3$ of thymine), 2.5–2.4 (m, 2H, H2'$^a$/H2'$^b$), 2.63 (t, 2H, —C$\underline{H}_2$—CH$_2$—, 3'-OH protecting group, 2.9 (t, 2H, ——CH$_2$—C$\underline{H}_2$—, 3'-OH protecting group), 2.9 (t, 2H, —C$\underline{H}_2$—CH$_2$—, 5'-OH protecting group), 3.04 (t, 2H, —CH$_2$—C$\underline{H}_2$—, 5'-OH protecting group), 3.04 (s, 3H, $R_3C$—OC$\underline{H}_3$), 3.45 (m, 2H, H5'$^a$/H5'$^b$), 3.77 (s, 12H, aryl-OC$\underline{H}_3$), 4.14 (m, 1H, H4'), 4.54 (s, 2H, —CO—C$\underline{H}_2$—O—), 5.47 (m, 1H, H3'), 6.43 (t, 1H, H1'), 7.37–6.7 (m, 26H, aryl-$\underline{H}$), 7.6 (s, 1H, H6), 8.21 (d, 2H, $O_2N$-aryl-$\underline{H}$, ortho), 8.9 (s, 1H, N—$\underline{H}$ of thymine). -$^{13}$C NMR (101 MHz, $CDCl_3$ and a trace of [$D_5$]pyridine): δ=11.66 (q, —C$\underline{H}_3$ of thymine), 27.4 (t, —C$\underline{H}_2$—CH$_2$—, 3'-OH protecting group), 30.26 (t, C$\underline{H}_2$—CH$_2$—, 5'-OH protecting group), 33.77 (t, —CH$_2$—C$\underline{H}_2$—, 3'-OH protecting group), 35.68 (t, —CH$_2$—C$\underline{H}_2$—, 5'-OH protecting group), 37.88 (t, C2'), 51.90 (q, $R_3C$—OC$\underline{H}_3$), 55.21, 55.27 (q, aryl-OC$\underline{H}_3$, 3'-OH and 5'-OH protecting group, position not defined) 63.74 (t, C5'), 72.74 (t, —CO—C$\underline{H}_2$—O—), 75.69 (d, C3'), 83.96 (d, C4'), 84.38 (d, C1'), 86.29, 87.05 (s, $R_3\underline{C}$—OCH$_2$—, 5'-OH protecting group, $R_3\underline{C}$—OCH$_3$, 3'-OH protecting group, position not defined), 111.49 (s, C5 of thymine), 112.29, 113.09, 113.37, 114.59, 121.81, 122.37, 128.07, 128.38, 128.93, 130.08, 130.18 (d, $\underline{C}$—H, aryl), 125.17 (d, $\underline{C}$—H, $O_2N$-aryl, ortho), 135.61 (d, C6 of thymine), 135.06, 135.4, 138.55, 142.89, 145.33, 147.57, 155.28 (s, aryl, quarternary), 150.37 (C2 of thymine), 157.3, 158.51 (s, $R_2\underline{C}$—OCH$_3$, and s, $R_2\underline{C}$—O—CH$_2$CO—: 3'-OH protecting group, aryl, position not defined), 158.84 (s, $R_2\underline{C}$—COCH$_3$, aryl, 5'-OH protecting group), 163.57 (s, C4 of thymine), 170.35 (s, —$\underline{C}$OOR, 5'-OH protecting group), 172.07 (s, —$\underline{C}$OOR, 3'-OH protecting group), 205.94 (s, —$\underline{C}$O—). -$^1$H$^1$H and $^1$H$^{13}$C 2D NMR spectra are determined (data not shown) -MS (FAB, pos mode) m/z (rel. intensity) m/z calculated for $C_{67}H_{65}N_3O_{17}$ (M$^+$). 1183, found: 1183 (4), 1152 (35, M—OCH$_3^+$), 1137 (2, M—NO$_2^+$), 496 (100, fragment M—OH$^+$ of compound 38). -Elementary Analysis (%): Found: C, 67.63/67.89; H, 5.63/5.69; N, 3.49/3.51; $C_{67}H_{65}N_3O_{17}$ requires C, 67.95; H, 5.53; N, 3.55.

Example 9
Aminolysis of Compound 40 with Aminopropyl CPG to Building Block 1

Compound 40 (0.160 g, 0.135 mmol) was dissolved in dry dioxane (0.311 ml) and dry pyridine (0.032 ml). A suspension of aminopropyl CPG (0.405 g, CPG-10–500, Biosyntech, Hamburg) in 1.27 ml dry N,N-dimethylformamide and 0.160 ml (0.116 g, 1.15 mmol) dry triethylamine was added and the suspension shaken during 21.5 h. An intensive yellow color indicated beginning reaction caused by released p-nitrophenolate ions. The suspension was shaken during 21.5 h. A ninhydrin test at this stage indicated the existence of free amino groups on the support. To acylate, "cap", these groups, dry triethylamine (0.030 ml) and acetic anhydride (0.090 ml) were added and the suspension was shaken for another 60 min. After this time a negative ninhydrin test was obtained. The support was washed successively with N,N-dimethylformamide, ethanol, dioxane, ether (100 ml each) and dried in vacuo. Analysis for the extent of 3'-OH protected nucleoside attached to the support was done spectrophotometrically. An accurately weighed sample was treated either with 5% dichloroacetic acid in dichloromethane (v/v) or with hydrazine reagent IV (table 1) followed by acidifying the solution with 40% trichloroacetic acid in dichloromethane (percentage by weight). The liquid phase was measured at 513 nm (extinction coefficient of an acid solution of the removed trityl derivate: ε=78600). Amount of nucleoside bound to the support 1:45.6 μmol/g.

Example 10
Syntheses of the Fully Deprotected Oligonucleotides d(TTTT) and d(TAGCT)

The apparatus for manual oligonucleotide synthesis consisted in a column type reactor fitted with a sintered glass fritt, a stopcock and a connection to a vacuum pump to remove solvents by suction or to dry the support just before the condensation step (step 3, table 2). Only this step was carried out under inert gas athmosphere (argon). The inert gas was introduced to the apparatus via an injection needle through a septum at the top of the apparatus. Another needle through the septum guaranteed equalizing of the gas pressure Notes and Descriptions of the Reagents and Solvents 1) For synthesis 0.0220 g of the support 1 with about 1 μmol loaded nucleoside was used.

2) For the synthesis of d(TTTT) 0.146 g amidite 2a was dissolved in 1.4 ml acetonitrile (DNA grade). For the synthesis of d(TAGCT) 0.0800 g of 2a–d each was dissolved in 0.8 ml each of acetonitrile (DNA grade).

3) Tetrazole reagent: 31.8 g 1-H-tetrazole in 1 l acetonitrile; GEN 905035.

4) Oxidation reagent: 4.3 g iodine in 1 l water/pyridine/tetrahydrofuran (THF), 9.05/0.41/90.54, v/v; GEN 905028.

5) Capping reagent 1: N-methylimidazole/pyridine/acetonitrile, 12/10/78, v/v, GEN 905027; capping reagent 2; acetic anhydride/acetonitrile, 12/88, v/v, GEN 905026. The tetrazole, oxidation and the capping reagents are purchased from PerSeptive Biosystems GmbH, Hamburg.

6) Hydrazine reagent: 0.5M hydrazine reagent IVb (table 1). Reagent of high quality have to be used: bidistilled water, acetic acid p.a. (Merck, Darmstadt No. 63), hydrazinium hydrate (Merck, Darmstadt No. 804608), pyridine p.a. (Merck, Darmstadt No. 7463)

7) TCA reagent: 40% trichloroacetic acid in dichloromethane (percentage by weight).

8) Amidite and tetrazole solutions and acetonitrile (DNA grade) to dissolve amidites and to carry out the last washing in step 2 (table 2) before the condensation were kept under molecular sieve 0.3 nm, freshly activated in a microwave oven, stored under argon and taken or added by syringes via septa.

9) Acetonitrile for washing steps only had to be "HPLC grade", except for the last washing before the condensation.

TABLE 2

Steps involved in one elongation cycle during synthesis.

| Step | Operation | Reagent | Volume (ml) | Duration (min) |
|---|---|---|---|---|
| 1 | Delaevulination | Hydrazine reagent | 0.7 | 60 |
| 2 | Washing | N,N-Dimethylformamide | 2 × 5 | |
| | | Acetonitrile | 2 × 5[a] | |
| | | Acetonitrile (DNA grade) | 1 × 5 | |
| 3 | Drying | High vacuum (then flushing with argon) | | 10 |
| 4 | Condensation | a) Amidite solution | 0.4 | 1[b] |
| | | | 0.8 | 3[c] |
| | | b) Tetrazole solution | 0.8[d] | 9[b] |
| | | | 1.6[d] | 10[c] |
| 5 | Washing | Acetonitrile | 2 × 5 | |
| 6 | Oxidation | Oxidation reagent | 1.65 | 1 |
| 7 | Washing | Acetonitrile | 2 × 5 | |

TABLE 2-continued

Steps involved in one elongation cycle during synthesis.

| Step | Operation | Reagent | Volume (ml) | Duration (min) |
|---|---|---|---|---|
| 8 | Capping | Capping reagent 1 | 1.25 | 1 |
| | | Capping reagent 2 | 1.25 | |
| 9 | Washing | Acentonitrile | 2 × 5 | |
| 10 | Drying | High Vacuum | | some min |

[a] before washing with acetonitrile (DNA grade) insert septum,
[b] in case of d(TTTT) synthesis,
[c] in case of d(TAGCT) synthesis
[d] add dropwise Sufficient contact between support and solvent or reagent was guaranteed by occasional gentle shaking, especially after addition of amidite solution and during the dropwise addition of the tetrazole reagent.

⅓ of the solution of step 1 (0.233 ml) was given in a 25 ml standard flask and filled up to the mark with the TCA reagent. The absorptions of the solutions of the elongation cycles were measured spectrophotometrically at 513 nm leading to the nucleoside loading of support 1 and to the yields of the condensation reactions.

Deprotection and Purifications of the Oligomers

A) d(TTTT) synthesis:

The support with the attached oligomer was washed with pyridine and the β-cyanoethyl groups were removed with tert-butyl amine reagent II (table 1). After washing the support with pyridine and acetonitrile and drying in vacuo, the oligomer was removed from the support by treating it with 80% acetic acid for 15 min. After lyophilization of the solution, the oligomer was purified by HPLC: the terminal 3'-OH protecting group (corresponding to the group of compound 29a in scheme 7) served here as purification handle. Treatment with 32% ammonia followed by lyophilisation led to the fully deprotected oligomer d(TTTT).-HPLC: Ret. time (min): 8.57, UV detection: λmax=266.1 and 217.7 nm.-MS (MALDI-TOF): theoretical mass: M+H+: 1155; found: 1154.

B) d(TAGCT) synthesis:

The oligomer was removed from the support by treatment with 80% acetic acid for 15 min. After lyophilisation, the base, the phosphate and the 3'-OH protection were removed by treatment with 0.5M DBU in acetonitrile leading directly to the fully deprotected d(TAGCT). The reagent was as evaporated in vacuo. -HPLC: Ret. time (min): 6.96, UV detection: λ max=259.0 and 216.5 nm. -MS (MALDI-TOF): M+H−: theoretical mass: 1478; found: 1477.

Deprotection Experiments with Model Compounds

The deprotection experiments with model compounds in solution were monitored by thin layer chromatography. The molar ratios of the deprotection reagents I–IV (table 1) to the model compounds were at least 100:1.

What is claimed is:

1. A process for generating a combinatorial library, comprising the steps of:

(a) preparing a plurality of immobilized molecules selected from a nucleoside and a nucleotide; wherein each molecule contains 3 reactive moieties, each reactive moiety being blocked by a blocking group, wherein the three blocking groups on each immobilized molecule are independently removable under three different conditions; and (b) removing each blocking group and derivatizing the resulting reactive moiety in a preprogrammed, regioselective manner; wherein each member of the plurality of immobilized molecules is uniquely derivatized at at least one reactive moiety with a unique substituent, thereby generating a combinatorial library.

2. A process of claim 1, wherein the reactive moieties are selected from OH, SH, $NH_2$, $CO_2H$, SOH, $SO_2H$, $SO_3H$, CHO, keto, phosphate, phosphite, phosphoamidite, halogen, CN, CNS, NCS and NCO.

3. A process of claim 1, wherein the immobilized molecules have been immobilized based on linkage to a solid support.

4. A process of claim 3, wherein the solid support is selected from beads, flat supports, wafers with pits, wafers without pits, wafers with channels, wafers without channels, bottom surface of a microtiter plate, and inner walls of a capillary.

5. A process of claim 4, wherein the beads are comprised of a material selected from polystyrene, polyamide, cellulose, agarose, dextran cross-linked with epichlorohydrin, silica gel, controlled pore glass (CPG), and polytetrafluoroethylene.

6. A process of claim 3, wherein the linkage is cleavable under acidic, alkaline, neutral or photolytic conditions.

7. A process of claim 6, wherein the linkage is selected from trityl ether, ester, β-benzoylpropionyl, levulinyl, disulfide and sulfenyl.

* * * * *